US005700660A

United States Patent [19]
Leonard et al.

[11] Patent Number: 5,700,660
[45] Date of Patent: Dec. 23, 1997

[54] POSITIONAL CONTROL OF SELENIUM INSERTION IN POLYPEPTIDES FOR X-RAY CRYSTALLOGRAPHY

[75] Inventors: Jack L. Leonard, Shrewsbury; Peter E. Newburger, Waban, both of Mass.

[73] Assignee: University of Masachusetts Medical Center, Worcester, Mass.

[21] Appl. No.: 473,496

[22] Filed: Jun. 7, 1995

Related U.S. Application Data

[63] Continuation-in-part of Ser. No. 277,492, Jul. 19, 1994, abandoned, which is a continuation-in-part of Ser. No. 66,680, May 24, 1993, abandoned.

[51] Int. Cl.⁶ .................................................. C12N 15/00
[52] U.S. Cl. ........................ 435/69.1; 378/73; 530/400
[58] Field of Search .......................... 435/69.1; 378/73; 530/400

[56] References Cited

U.S. PATENT DOCUMENTS 5,272,078 12/1993 Larsen et al. ........................... 435/189

FOREIGN PATENT DOCUMENTS

WO 92/13077 8/1992 WIPO.

OTHER PUBLICATIONS

Alberts, *Molecular Biology of the Cell*, pp. 179–180 (1983).
Baron et al., Abstract, p. 38, The Fifth Int'l Symp. on Selenium in Biology in Biology & Medicine, Jul. 20–23, 1992, Vanderbilt University School of Medicine, Nashville, TN.
Berg et al., *J. of Biological Chemistry*, 266:22386–22391, (1992).
Berry et al., Abstract, pp. 2, 39, the Fifth Int'l Symp. on Selenium in Bio. & Medicine, Jul. 20–23, 1992 Vanderbilt University School of Medicine, Nashville, TN.
Berry et al., *Nature*, 349:438–440, (1991).
Berry et al., *Nature*, 353:273–276, (1991).
Berry et al., *Endocrinology*, 131:1848–1852, (1992).
Böck, Abstract, p. 3, The Fifth Int'l Symp. on Selenium in Bio. and Medicine, Jul. 20–23, 1992, Vanderbilt University School of Medicine, Nashville, TN.
Böck et al., *TIBS*, 16:463–467, (1991).
Burk, *Essential and Toxic Trace Elements in Human Health and Disease:An Update*, Wiley–Liss, Inc., pp. 181–190, (1993).
Chada et al., *Genomics*, 6:268–271, (1990).
Chada et al., *Blood*, 74:2535–2541, (1989).
Chada et al., *Oxy–Radicals in Molecular Biology and Pathology*, pp. 273–288 Alan R. Liss, Inc. (1988).
Chambers et al., *The EMBO Journal*, 5:1221–1227, (1986).
Chanoine et al., *Endrocrinology*, 131:1787–1792, (1992).
Chu et al., *Nucleic Acids Research*, 18:1531–1539, (1990).
Choi et al., Abstract, p. 40, The Fifth Int'l Symp. on Selenium in Bio. & Medicine, Jul. 20–23, 1992 Vanderbilt University School of Medicine, Nashville, TN.
Esworthy et al., *Archives of Biochemistry and Biophysics*, 286:330–336, (1991).
Hatfield, Abstract, p. 4, The Fifth Int'l Symp. in Bio. & Medicine, Jul. 20–23, 1992 Vanderbilt University School of Medicine, Nashville, TN.
Hatfield, *TIBS*, pp. 201–204, (May 1985).
Hawkes et al., *Biochimica et Biophysica Acta*, 699:183–191, (1982).
Hendrickson et al., *Proc. Natl. Acad. Sci.*, USA 86:2190–2194 Apr. (1989).
Hendrickson et al., *The Embo Journal*, 9:1665–1672, (1990).
Hendrickson et al., *Science*, 254:51–58 Oct. (1991).
Hendrickson et al., *Transactions of the American Crystallographic Association*, 21:11–21 Oct. (1985).
Herrman, *Biochimica et Biophysica Acta*, 500:61–70, (1977).
Herzog et al., Abstract, p. 44, The Fifth Int'l Symp. in Bio. & Medicine, Jul. 20–23, 1992 Vanderbilt University School of Medicine, Nashville, TN.
Hill et al., *The Journal of Biological Chemistry*, 266:10050–10053, (1991).
Hill et al., *Biochemcial and Biophysical Research Communications*, 185:260–263, (1992).
Ho et al., *Nucleic Acids Research*, 16:5207, (1988).
Huber et al., *Biochim. Biophys. Acta*, 141:587–599 (1967).
Jaenisch, *Science*, 240:1468–1474, (Jun. 1988).
Knight et al., *J. Nutrition*, 117:732–738, (1987).
Lee et al., *Proc. Natl. Acad. Sci. USA*, 84:6384–6388, (1987).
Lee et al., *The Journal of Biological Chemistry*, 264:9724–9727, (1989).
Leonard et al., *Biochimica et Biophysica Acta*, 787:122–130, (1984).
Mizutani et al., Abstract, p. 48, The Fifth Int'l Symp. on Selenium in Bio. & Medicine, Jul. 20–23, 1992, Vanderbilt University School of Medicine, Nashville, TN.
Mullenbach et al. *Nucleic Acids Research*, 15:5484, (1987).
Odom, *Structure and Bonding* 54:1–26 (1983).
Read et al., *The Journal of Biological Chemistry*, 265:17899–17905, (1990).

(List continued on next page.)

*Primary Examiner*—Robert A. Wax
*Assistant Examiner*—Enrique D. Longton
*Attorney, Agent, or Firm*—Fish & Richardson P.C.

[57] ABSTRACT

The invention provides methods for determining the structure of a polypeptide by a) transfecting a cell with (i) a first nucleic acid encoding the polypeptide, wherein at least one, specific codon of mRNA transcribed from the first nucleic acid is replaced by the codon UGA, and (ii) a second nucleic acid, operably linked to the first nucleic acid, that directs the translation of the UGA codon as selenocysteine only when the cell can obtain selenium from the medium in which it is grown; b) growing the cell in selenium-containing growth medium under conditions in which the cell incorporates at least one selenocysteine residue into the polypeptide at a specific location; c) isolating the polypeptide from the cell or the growth medium; d) forming a crystal of the polypeptide; and e) performing X-ray crystallography on the crystal, wherein the selenocysteine residue is used to determine the structure of the polypeptide.

16 Claims, 11 Drawing Sheets

OTHER PUBLICATIONS

Ryu et al., *Nature,* 348:419–423, Nov. (1990).

Speier et al., *The Journal of Biological Chemistry,* 260:8951–8955, (1985).

Stadtman et al., *FASB J.,* 1(5)375–379, Nov. (1987).

Sunde et al., Abstract, p. 15, The Fifth Int'l Symp. on Selenium in Bio. & Medicine, Jul. 20–23, 1992, Vanderbilt University School of Medicine, Nashville, TN.

Takahashi, et al., *Blood,* 68:640–645, (1986).

Toyoda et al., *Biochimica et Biophysica Acta,* 1008:301–308, (1989).

Weaver et al., *Genetics,* pp. 451–457, Wm. C. Brown Publishers, Dubuque, Iowa, (1989).

Zinoni et al., *Proc. Natl. Acad. Sci. USA,* 87:4660–4664, (1990).

Syed et al. (1993) Crystal Structure of Selenosubtilisin at 2.0-A Resolution. Biochemistry, vol. 32, pp. 6157–6164.

Epp et al. (1983) The Refined Structure of the Selenoenzyme Glutathione Peroxidase at 0.2–nm Resolution. Eur. J. Biochem. vol. 133, pp. 51–69.

```
GCGCC                                                                5

ATG TGT GCT GCT CGG CTA GCG GCG GCG GCG GCC CAG TCG GTG TAT GCC     53
Met Cys Ala Ala Arg Leu Ala Ala Ala Ala Ala Gln Ser Val Tyr Ala
1               5                   10                  15

TTC TCG GCG CGC CCG CTG GCC GGC GGG GAG CCT GTG AGC CTG GGC TCC    101
Phe Ser Ala Arg Pro Leu Ala Gly Gly Glu Pro Val Ser Leu Gly Ser
            20                  25                  30

CTG CGG GGC AAG GTA CTA CTT ATC GAG AAT GTG GCG TCC CTC TGA GGC    149
Leu Arg Gly Lys Val Leu Leu Ile Glu Asn Val Ala Ser Leu SeC Gly
        35                  40                  45

ACC ACG GTC CGG GAC TAC ACC CAG ATG AAC GAG CTG CAG CGG CGC CTC    197
Thr Thr Val Arg Asp Tyr Thr Gln Met Asn Glu Leu Gln Arg Arg Leu
        50                  55                  60

GGA CCC CGG GGC CTG GTG GTG CTC GGC TTC CCG TGC AAC CAG TTT GGG    245
Gly Pro Arg Gly Leu Val Val Leu Gly Phe Pro Cys Asn Gln Phe Gly
65              70                  75                  80

CAT CAG GAG AAC GCC AAG AAC GAA GAG ATT CAG AAT TCC CTC AAG TAC    293
His Gln Glu Asn Ala Lys Asn Glu Glu Ile Gln Asn Ser Leu Lys Tyr
            85                  90                  95

GTC CGG CCT GGT GGT GGG TTC GAG CCC AAC TTC ATG CTC TTC GAG AAG    341
Val Arg Pro Gly Gly Gly Phe Glu Pro Asn Phe Met Leu Phe Glu Lys
            100                 105                 110

TGC GAG GTG AAC GGT GCG GGG GCG CAC CCT CTC TTC GCC TTC CTG CGG    389
Cys Glu Val Asn Gly Ala Gly Ala His Pro Leu Phe Ala Phe Leu Arg
        115                 120                 125

GAG GCC CTG CCA GCT CCC AGC GAC GAC GCC ACC GCG CTT ATG ACC GAC    437
Glu Ala Leu Pro Ala Pro Ser Asp Asp Ala Thr Ala Leu Met Thr Asp
        130                 135                 140

CCC AAG CTC ATC ACC TGG TCT CCG GTG TGT CGC AAC GAT GTT GCC TGG    485
Pro Lys Leu Ile Thr Trp Ser Pro Val Cys Arg Asn Asp Val Ala Trp
145                 150                 155                 160

AAC TTT GAG AAG TTC CTG GTG GGC CCT GAC GGT GTG CCC CTA CGC AGG    533
Asn Phe Glu Lys Phe Leu Val Gly Pro Asp Gly Val Pro Leu Arg Arg
            165                 170                 175

TAC AGC CGC CGC TTC CAG ACC ATT GAC ATC GAG CCT GAC ATC GAA GCC    581
Tyr Ser Arg Arg Phe Gln Thr Ile Asp Ile Glu Pro Asp Ile Glu Ala
            180                 185                 190

CTG CTG TCT CAA GGG CCC AGC TGT GCC TAG                            611
Leu Leu Ser Gln Gly Pro Ser Cys Ala AM
            195                 200

GGCGCCCCTC CTACCCCGGC TGCTTGGCAG TTGCAGTGCT GCTGTCTCGG GGGGGTTTTC   671
ATCTATGAGG GTGTTTCCTC TAAACCTACG AGGGAGGAAC ACCTGATCTT ACAGAAAATA   731
CCACCTCGAG ATGGGTGCTG GTCCTGTTGA TCCCAGTCTC TGCCAGACCA AGGCGAGTTT   791
CCCCACTAAT AAAGTGCCGG GTGTCAGCAA AAAAAAAAA A                        832
(SEQ ID NO: 1)
```

FIG. 1

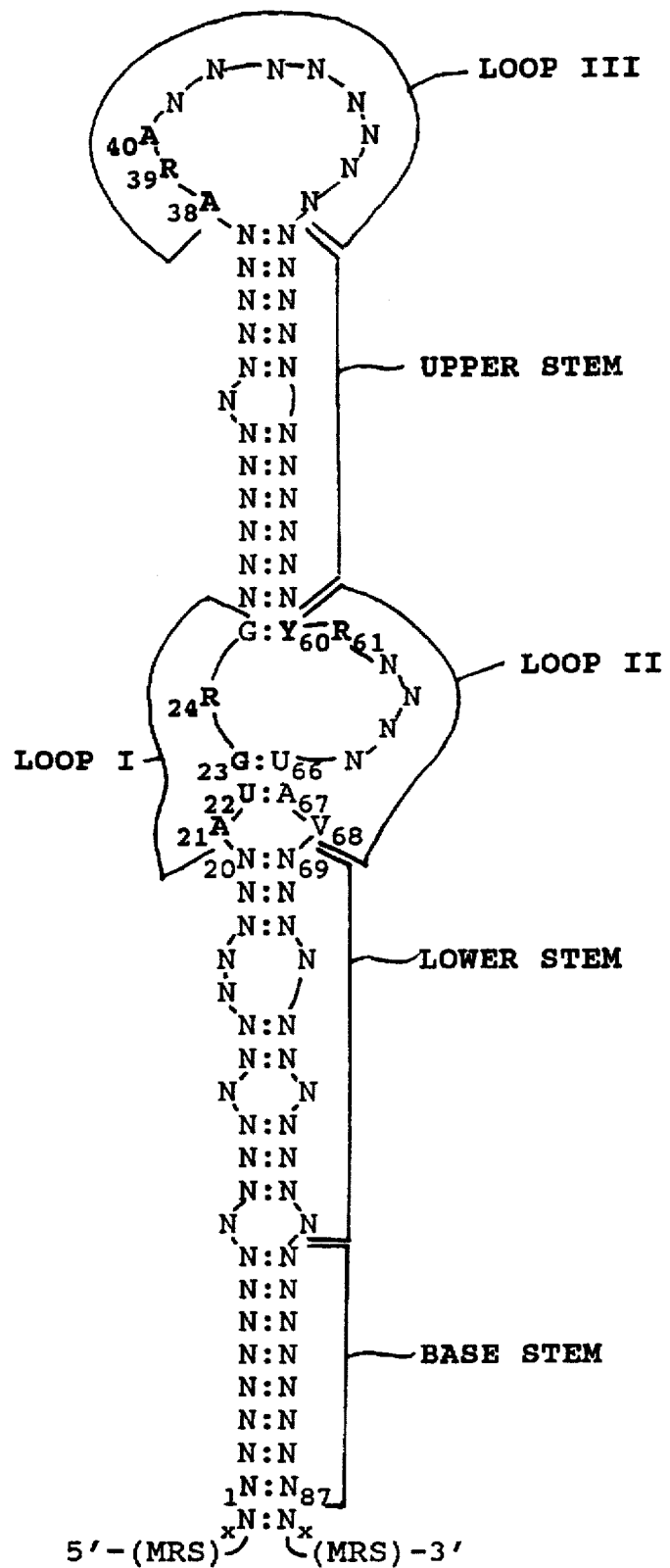
FIG. 2 (SEQ ID NO: 5)

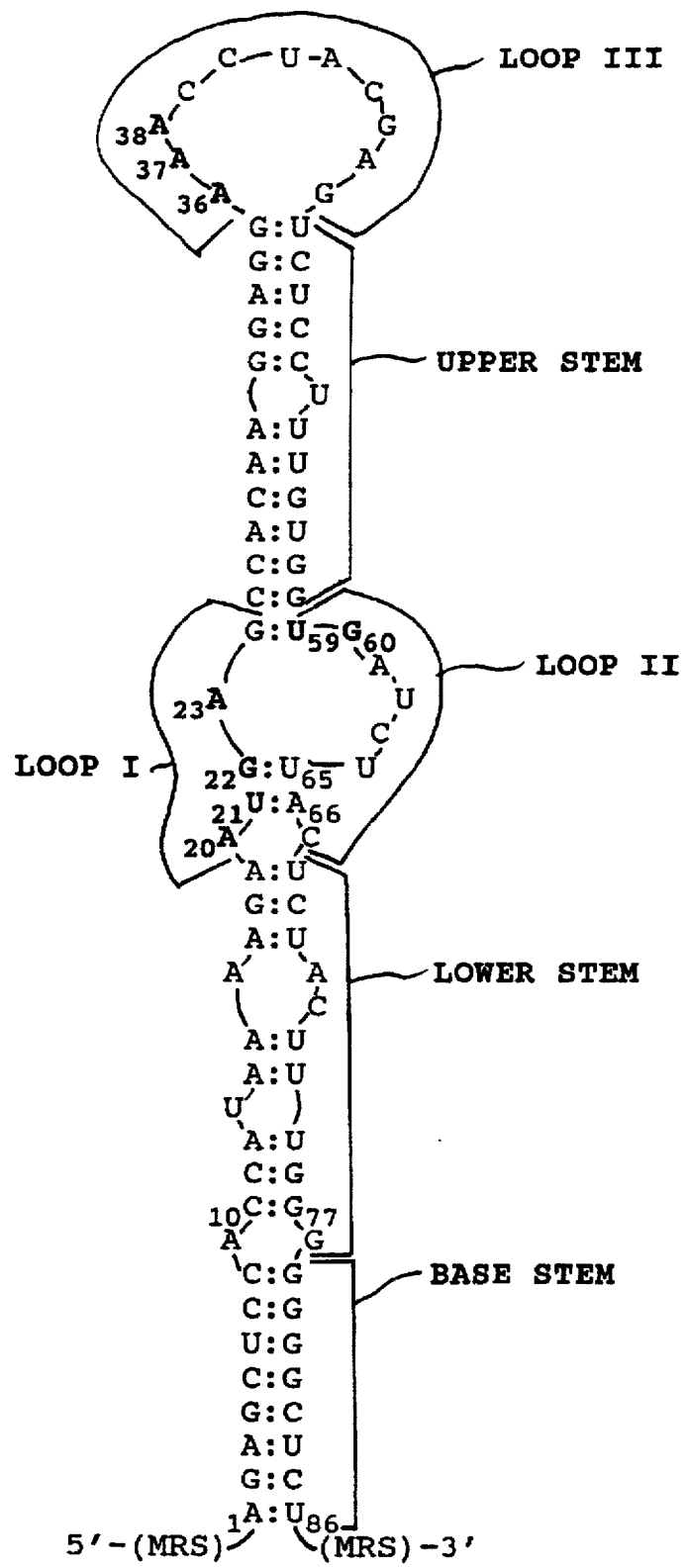
FIG. 3 (SEQ ID NO: 6)

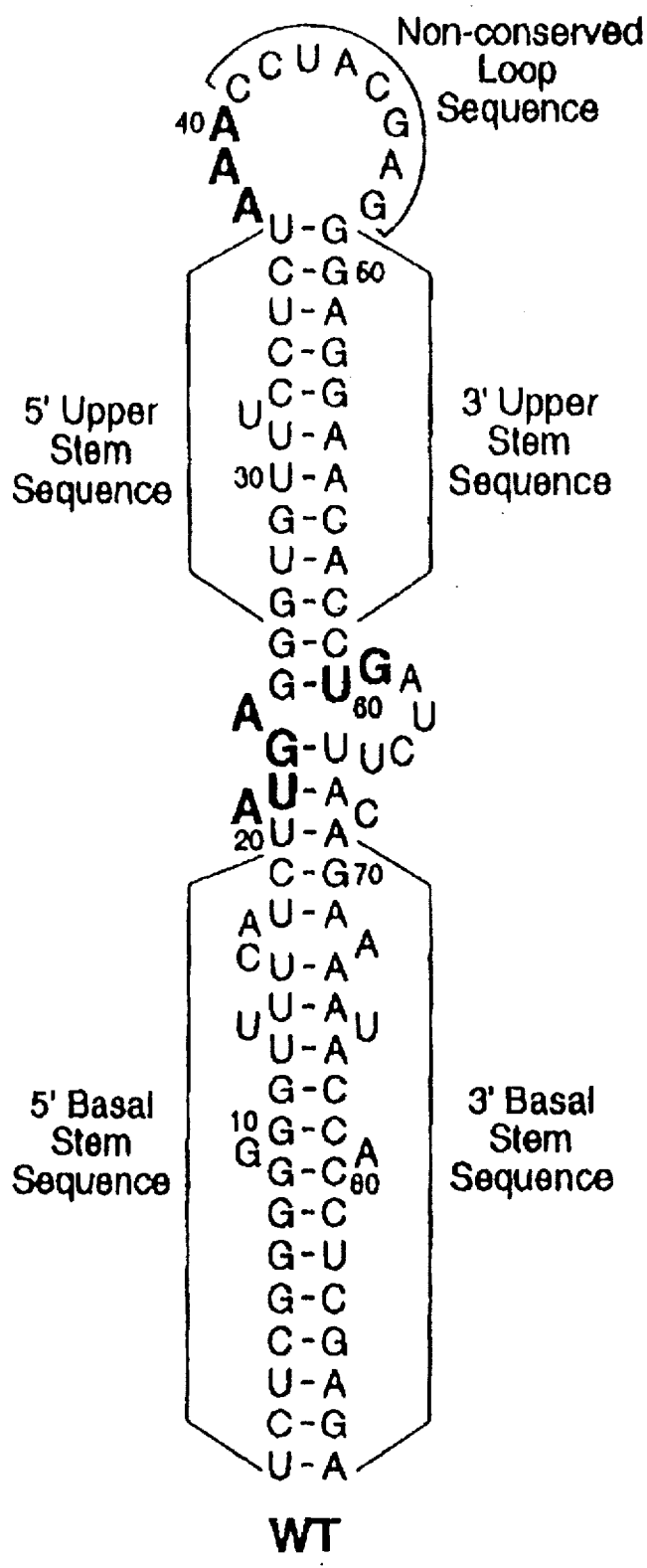
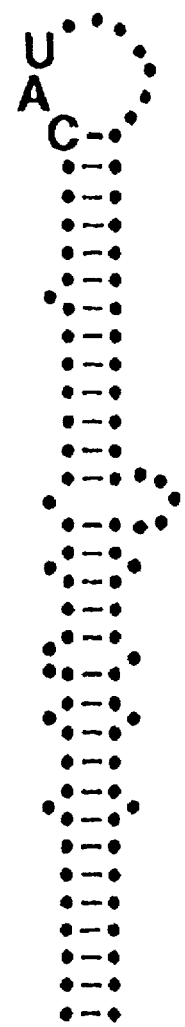
WT
FIG. 4A (SEQ ID NO: 7)
AAA→CAU
FIG. 4B

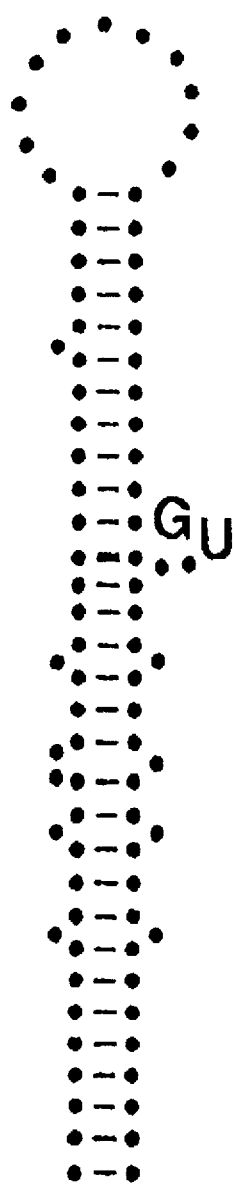
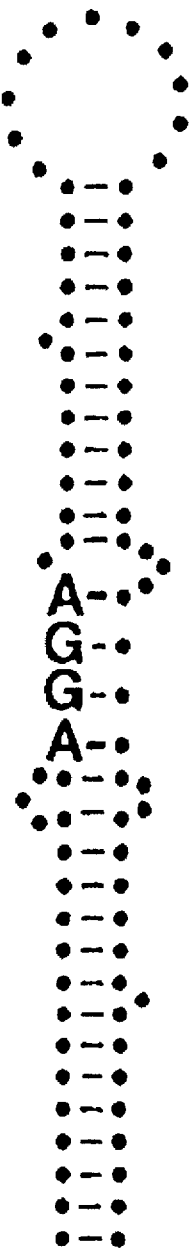
UG→GU  AUGA→AGGA
FIG. 4C  FIG. 4D

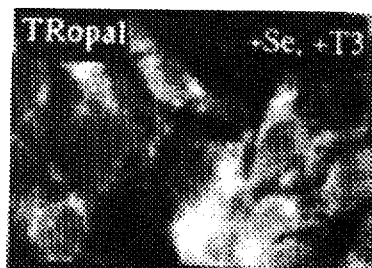
FIG. 9A
FIG. 9B
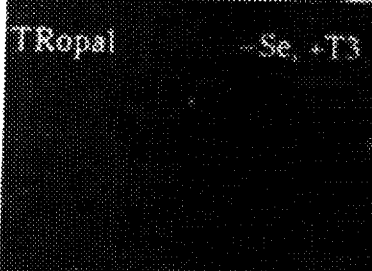
FIG. 9C
FIG. 9D
FIG. 9E
FIG. 9F

POSITIONAL CONTROL OF SELENIUM INSERTION IN POLYPEPTIDES FOR X-RAY CRYSTALLOGRAPHY

This application is a continuation-in-part of U.S. Ser. No. 08/277,492, filed Jul. 19, 1994 now abandoned, which is a continuation-in-part of U.S. Ser. No. 08/066,680, filed May 24, 1993 now abandoned.

STATEMENT OF FEDERALLY SPONSORED RESEARCH

Partial funding of the work described herein was provided by the United States Public Health Service Grants DK41625 and DK38772 and NIH Grants JLL and PEN. The U.S. government has certain rights in this invention.

BACKGROUND OF THE INVENTION

The invention relates to the controlled incorporation of selenocysteine residues into polypeptides and to uses of the resultant selenopolypeptides in X-ray crystallography.

Selenium is used by certain organisms to regulate the expression of selenoproteins. Selenoproteins are a unique group of polypeptides that are found in both prokaryotes and eukaryotes and contain the unusual amino acid, selenocysteine. This small group of proteins includes the prokaryotic enzymes in the formate dehydrogenase family, and several eukaryotic polypeptides including the glutathione peroxidase (GPx) enzymes, type I iodothyronine deiodinase, and selenoprotein P. In all of these proteins, selenocysteine incorporation is directed by the universal termination codon, UGA (see, Bock et al., *Trends Biochem. Sci.* 16, 463–467, 1991) and requires both a unique selenocysteine-charged tRNA$^{Ser[Sec]}$ containing the UCA anticodon (Hawkes et al., *Biochim. Biophys. Acta* 699, 183–191, 1982), and specific secondary structural elements in the mRNA (Berry et al., *Nature* 353, 273–276, 1991).

Selenocysteine synthesis is also unique, and the amino acid is formed by the enzyme-catalyzed substitution of selenium for the phosphate of a phosphoserine-charged tRNA$^{Ser[Sec]}$ (see, e.g., Lee et al., *Mol. Cell. Biol.* 10, 1940–1949, 1990). Since selenium is essential to synthesize selenocysteine, removal of selenium from the diet or culture medium leads to a marked reduction in the cellular levels of all selenoproteins (see, e.g., Chanoine et al., *Endocrinology* 131, 479–484, 1992) due to an inability to translate the UGA codon. Thus, the selenium supply determines whether the UGA triplet in a selenoprotein transcript serves as a selenocysteine codon or a stop signal.

Bacteria and mammals differ in the mechanisms by which the translational apparatus interprets a UGA triplet as a selenocysteine codon or as a signal for chain termination. In the mRNA encoding *E. coli* formate dehydrogenase, selenocysteine incorporation at the UGA codon depends on a 40-nucleotide stem-loop located immediately downstream from the UGA and on several critical bases located in the middle of this stem-loop (Zinoni et al., *Proc. Natl. Acad. Sci. (USA)* 87, 4660–4664, 1990; Heider et al., *J. Bacteriology* 174, 659–663, 1992). In mammalian mRNA, chain elongation at a UGA codon also depends upon stem-loop structure(s), but they are located in the 3' untranslated region (3'UTR) of selenoprotein transcripts and have been identified as the "selenocysteine-insertion sequence" (SECIS) (Berry et al., 1991) or the "selenium translation element" (STE).

X-ray crystallography is used to determine the three-dimensional structure of polypeptides, but is often hampered by the inability of the investigator to unambiguously identify specific regions of the polypeptide without iterative, computer intensive calculations of repetitive X-ray diffraction patterns. Heavy atoms, having an atomic mass of greater than 20, are often added to the polypeptide during crystallization in an attempt to provide a point of reference, since these atoms provide unique signature(s) in multi-wavelength anomalous diffraction (MAD) and multiple isomorphous replacement (MIR) analysis. However, the heavy atoms are added to the crystal randomly, or at most or all locations of a certain amino acid throughout the polypeptide, e.g., a replacement of all methionines in a protein with a selenomethionine (Hendrickson et al., *EMBO J.*, 9:1665–1672, 1990).

SUMMARY OF THE INVENTION

The invention is based on the discovery that a particular secondary structure and only three, short, 2 to 4 nucleotide segments in the selenium translation element (STE) are necessary and sufficient for the STE to enable chain elongation at a UGA codon. For example, as described in detail below, in the STE element of the mammalian cellular glutathione peroxidase gene, GPX1, deletions or substitution mutations in any of the three short sequence elements severely diminishes expression of full-length glutathione peroxidase.

Based on this discovery, the invention includes the creation of synthetic or artificial STE elements that can be used to substitute the unique amino acid selenocysteine (SeCys), which contains the heavy atom selenium, for one or more amino acids at user-defined, specific locations in a target polypeptide, e.g., a heterologous polypeptide, that is to be analyzed by X-ray crystallography to determine its three-dimensional structure. The crystallographic methods of the invention take advantage of the chemical and biophysical properties of organic selenium (Odom, J. D. *Structure and Bonding*, 54, 1–26, 1983), and the controlled incorporation of selenocysteine into the polypeptide provides a much better target for X-ray crystallography analysis than the naturally occurring polypeptide.

In particular, we have overcome the inability in known methods to limit the position of a heavy atom to a defined, single position on a polypeptide, by providing the means to integrate the heavy atom, selenium, in the polypeptide chain in the form of a selenocysteine residue. This ability provides a known point-of-reference in the polypeptide that can be readily identified by multiple isomorphous replacement (MIR) and/or multi-wavelength anomalous diffraction (MAD) analysis, and allows physical identification of that amino acid in the crystal under study.

For example, MIR is a standard crystallographic technique that involves the addition of a heavy atom, e.g., an electron dense atom such as Pt, Au, Hg, Pd, or U, to a polypeptide crystal. However, the site of heavy atom addition within the crystallized polypeptide is generally unknown until after time-consuming crystallographic analysis. In some cases, it is impossible to add a heavy atom to a desired site within a polypeptide crystal. In contrast, the present invention features methods by which the electron-dense atom selenium, in the form of selenocysteine, can be targeted to one or more predetermined sites within a polypeptide prior to crystallographic analysis. Such a method greatly assists the crystallographic analysis of polypeptides. For example, several crystals of the same polypeptide can be made in which each crystal has a different selenocysteine substitution, an advantage not obtainable by conventional MIR techniques.

In general, a polypeptide is suitable for crystallographic analysis by a method of the invention if: 1) the nucleotide sequence of the gene encoding the polypeptide is known, and 2) the selenopolypeptide can be isolated and crystallized. A selenopolypeptide can be isolated and crystallized by well-known techniques.

The selenocysteine residue is preferably substituted for a naturally occurring cysteine, or at any site in which substitution of a selenocysteine residue does not alter the structure and function of the polypeptide, e.g., at a serine residue. Such amino acids can be identified by means well known to those skilled in the art, and will usually occur at positions that are not involved in the catalytic or binding activity of the protein (as determined for example by mutational analysis), or at positions considered critical for the structural integrity of the polypeptide.

In another embodiment, a selenocysteine residue is incorporated at a site in a polypeptide in which the substitution is known to alter the structure and/or function of the polypeptide to help determine the biological function of the polypeptide, e.g., to aid in identification of a polypeptide domain, an active site, or a binding site for a drug or another polypeptide.

Accordingly, the invention features a method for determining the structure of a polypeptide by a) transfecting a cell with (i) a first nucleic acid encoding the polypeptide, wherein at least one, specific codon of mRNA transcribed from the first nucleic acid is replaced by the codon UGA, and (ii) a second nucleic acid operably linked to the first nucleic acid, the second nucleic acid directing the translation of the UGA codon as selenocysteine only when the cell can obtain selenium from the medium in which the cell is grown; b) growing the cell in selenium-containing growth medium under conditions in which the cell incorporates at least one selenocysteine residue into the polypeptide at a specific location; c) isolating the polypeptide from the cell or the growth medium; d) forming a crystal of the polypeptide; and e) performing X-ray crystallography on the crystal, wherein the selenocysteine residue is used to determine the structure of the polypeptide.

The first and second nucleic acids can be introduced into and maintained in the cell in a recombinant vector that is capable of autonomously replicating in the cell according to standard techniques. To induce expression of the heterologous polypeptide, the cell culture medium typically contains between 1 and 50 ng/ml, preferably 2 to 40 ng/ml, and most preferably 5 to 25 ng/ml of selenium. The selenium may be present as sodium selenite or another soluble, oxidized form of selenium, for example, sodium selenate.

The polypeptide encoded by the first nucleic acid can be any desired polypeptide for which the nucleotide sequence is known. Methods of modifying the polypeptide to incorporate a selenocysteine amino acid residue are described herein. The UGA codon is preferably introduced into the first nucleic acid by site-directed mutagenesis using standard techniques.

In another embodiment of the method, at least two, specific codons of mRNA transcribed from the first nucleic acid are each replaced by the codon UGA, and the cell incorporates at least two selenocysteine residues into the polypeptide at specific locations, at least two of the selenocysteine residues are combined to form a selenocystine residue, and the selenocystine residue is used to determine the structure of the polypeptide in the X-ray crystallography.

Prior to forming a polypeptide crystal, the selenocysteine residue can be modified to form a selenide, selenoxide, seleninic acid, selenonic acid, selenone, or a seleno-sulfur group, and the modified selenocysteine residue can then be used in X-ray crystallography to determine the structure of the polypeptide.

The X-ray crystallography can involve multi-wavelength anomalous diffraction analysis, and the X-rays used in the X-ray crystallography can have wavelengths between about 0.3 to 3.0 Angstroms, and be produced by synchrotron radiation.

In particular embodiments, the second nucleic acid is derived from approximately 90 contiguous nucleotides from the 3' untranslated region of a gene encoding a naturally occurring mammalian selenoprotein, e.g., human glutathione peroxidase (GPx), and the second nucleic acid includes a nucleotide sequence substantially identical to nucleotides 654 to 740 of FIG. 1 (SEQ ID NO:1), which shows the complete nucleotide and amino acid sequences of GPx.

In another embodiment, the second nucleic acid is synthetically derived and includes a continuous stretch of at least 79 nucleotides having three stem elements, each having a 5' half and a 3' half, and three loop elements, each having a 5' end and a 3' end, wherein the stem elements comprise a) a base stem including at least 16 nucleotides in 8 complementary pairs of nucleotides, b) a lower stem including at least 16 nucleotides in 8 complementary pairs of nucleotides, the first nucleotide of the 5' half of the lower stem being bound to the last nucleotide of the 5' half of the base stem, and the first nucleotide of the 3' half of the lower stem being bound to the last nucleotide of the 3' half of the base stem, and c) an upper stem including at least 22 nucleotides in 11 complementary pairs of nucleotides, wherein the loop elements comprise d) a first loop consisting of 5'-AUGRG-3' (SEQ ID NO:2), the 5'-A being bound to the last nucleotide of the 5' half of the lower stem and the 3'-G being bound to the first nucleotide of the 5' half of the upper stem, e) a second loop consisting of 5'-YRNNNNUAV-3' (SEQ ID NO:3), the 5'-Y being bound to the first nucleotide of the 3' half of the upper stem and the 3'-V being bound to the last nucleotide of the 3' half of the lower stem, and f) a third, apical loop consisting of 5'-ARANNNNNNNN-3' (SEQ ID NO:4), the 5'-A being bound to the last nucleotide of the 5' half of the upper stem and the 3'-N being bound to the last nucleotide of the 3' half of the upper stem, and wherein each A is adenine, G is guanine, N is adenine, guanine, cytosine, or uracil, R is guanine or adenine, U is uracil, V is any nucleotide except thymidine or uracil, and Y is uracil or cytosine.

The second nucleic acid can further include a first mutually exclusive multiple cloning site tail attached to the first nucleotide of the 5' half of the base stem and a second mutually exclusive multiple cloning site tail attached to the first nucleotide of the 3' half of the base stem.

In a further embodiment, the second nucleic acid is synthetically derived, and includes a continuous stretch of 87 nucleotides, wherein a) nucleotides 1 to 8 are complementary to nucleotides 87 to 80, respectively, and when base-paired together form a base stem consisting of 16 nucleotides in 8 complementary pairs of nucleotides, b) nucleotides 9 to 20 and 69 to 79 when base-paired together form a lower stem consisting of at least 8 complementary pairs of nucleotides, c) nucleotides 21 to 25 are 5'-$A_{21}U_{22}G_{23}R_{24}G_{25}$-3' (SEQ ID NO:2) and form a first loop, d) nucleotides 60 to 68 are 5'-$Y_{60}R_{61}N_{62}N_{63}N_{64}N_{65}U_{66}A_{67}V_{68}$-3' (SEQ ID NO:3) and form a second loop, e) nucleotides 26 to 37 and nucleotides 49 to 59 when base-paired together form an upper stem of at least 11 complementary pairs of nucleotides, and f) nucleotides 38-48 are non-complementary and are 5'-$A_{38}R_{39}A_{40}N_{41}N_{42}N_{43}N_{44}N_{45}N_{46}N_{47}N_{48}$-3' (SEQ ID NO:4) and form a third, apical loop, and wherein A is adenine, G is guanine, N is adenine, guanine, cytosine, or uracil, R is guanine or adenine, U is uracil, V is any nucleotide except thymidine or uracil, and Y is uracil or cytosine.

In particular embodiments, the second nucleic acid has the sequence of FIG. 2 (SEQ ID NO:5) or the sequence of FIG. 3 (SEQ ID NO:6).

The invention also features methods by which a binding partner of a polypeptide can be detected. By "binding partner" is meant a synthetic or naturally occurring molecule that can non-covalently bind to a polypeptide. For example, a binding partner can be a naturally-occurring polypeptide, e.g., a growth factor, a hormone factor, a transcription factor, or a peptide hormone; a naturally-occurring molecule, e.g., asteroid hormone, or a cyclic nucleotide such as cAMP; or a synthetic polypeptide, or a synthetic, non-proteinaceous molecule, e.g., an antiviral drug or enzyme transition-state inhibitor. In general, a binding partner is combined with a selenopolypeptide of the invention under conditions that allow non-covalent binding of the binding partner with the selenopolypeptide. The combined pair is then crystallized and analyzed by X-ray crystallography using standard techniques.

The cell used to express the polypeptides of the invention can be any eukaryotic cell that is capable of being maintained in cell culture, e.g. a mammalian cell, a yeast cell, or an insect cell.

By "heterologous" nucleic acid is meant a nucleic acid which is partly or entirely foreign to the cell or animal in which it is introduced, or a nucleic acid which is homologous to an endogenous gene of the cell or animal with the exception that the heterologous protein contains selenocysteine substituted for at least one amino acid.

As used herein, the term "operably linked" means that the contiguous stretch of nucleotides which form the stem-loop secondary structure is in sufficient proximity with the nucleic acid encoding the protein to allow translation of any UGA codon in the protein to be translated as selenocysteine. Preferably, the stem-loop is inserted in the 3' untranslated region of the mRNA molecule encoding the polypeptide; preferably within 2000 nucleotides of the UGA codon, more preferably within 400 to 1500 nucleotides, and most preferably within 500 to 1200 nucleotides.

"Homologous," as used herein, refers to the sequence similarity between two polypeptide molecules or two nucleic acid molecules. When a position in both of the two compared sequences is occupied by the same nucleotide base or amino acid subunit, then the molecules are homologous at that position. Thus, by "substantially homologous" is meant a nucleotide or amino acid sequence that is largely, i.e. 90 percent, but not wholly homologous.

By "heterologous" polypeptide is meant a polypeptide that is partly or entirely foreign to the cell in which it is expressed.

An "isolated polypeptide" is a polypeptide separated from components of the cell with which it is naturally associated. Typically, an isolated polypeptide is purified to at least 95% of the total protein (by mole fraction) in a sample. Preferably, the isolated polypeptide is 100% of the total protein in a sample (by mole fraction).

By "multi-wavelength anomalous diffraction" (MAD) is meant a crystallographic technique in which X-ray diffraction data are collected at several different wavelengths from a single crystal containing a heavy atom (or heavy atoms) with absorption edges near the energy of incoming X-ray radiation. The resonance between X-rays and electron orbitals leads to differences in X-ray scattering that provide a solution of the crystallographic phase problem for a particular polypeptide. A detailed discussion of MAD analysis can be found in Hendrickson, *Trans. Am. Crystallogr. Assoc.*, 21:11 (1985); Hendrickson et al., *EMBO J.*, 9:1665 (1990); and Hendrickson, *Science*, 4:91 (1991).

By "synchrotron radiation" is meant X-ray radiation emitted by the acceleration of electrons as they are bent by magnetic fields at electron storage rings. Unlike X-rays generated in a standard X-ray generator, synchrotron radiation is extremely intense and generally includes x-ray wavelengths between about 0.3 and 3.0 Å.

By "multiple isomorphous replacement" (MIR) is meant a method of determining phase for diffracted X-rays by the introduction of heavy atoms into a polypeptide crystal. In this method, diffraction data is collected at a single wavelength from different crystals. Intensity differences result from the presence or absence of heavy atoms at different locations within each crystal, but these locations are determined only after X-ray analysis is completed.

By "heavy atom" is meant an element with an atomic number of at least 20. Selenium, in the form of selenocysteine is the heavy atom used in the present invention. Other heavy atoms used in prior art X-ray crystallography methods are Hg, Pt, Au, U, and Pb.

Unless defined otherwise, all technical terms and scientific terms used herein have the same meaning as commonly understood by one of ordinary skill in the art to which this invention belongs. Although any methods and materials similar or equivalent to those described herein can be used in the practice or testing of the present invention, the preferred methods and materials will now be described. All patents, patent applications, and publications mentioned herein are incorporated by reference. In addition, the materials, methods and examples are illustrative only and not intended to be limiting.

The methods of the present invention provide several advantages. First, SeCys has all of the biological properties of the amino acid residue Cys, and thus substitution of SeCys for Cys does not result in a significant alteration in the normal biological activity of the transfected gene product. Second, a transfected gene product which contains SeCys can be readily distinguished from native cellular proteins via its heightened reactivity toward nucleophilic reagents, or by $^{75}$Se incorporation.

Other features and advantages of the invention will be apparent from the following detailed description, and from the claims.

DETAILED DESCRIPTION

The drawings will first be briefly described.
Drawings FIG. 1 is a schematic depicting the nucleotide sequence of the human glutathione peroxidase gene including the 3' untranslated region (UTR) (SEQ ID NO:1).

FIG. 2 is a schematic diagram depicting an "optimized" STE (SEQ ID NO:5).

FIG. 3 is a schematic diagram depicting a particular synthetic STE (SEQ ID NO:6).

FIGS. 4A to 4D are schematic diagrams of computer (FOLDRNA program) predictions of the sequence and secondary structure of the selenium translation element (STE) of wild-type human glutathione peroxidase (FIG. 4A) (SEQ ID NO:7), and various mutated forms, AAA→CAU (4B), UG→GU (4C), and AUGA→AGGA (4D).

FIGS. 9A to 9F are a series of immunofluorescence micrographs showing how selenium-regulated expression of the opal mutant of TRβ1 determines the hormone-dependent expression of myelin basic protein.

SELENOCYSTEINE-CONTAINING PROTEINS

Figure 7A:
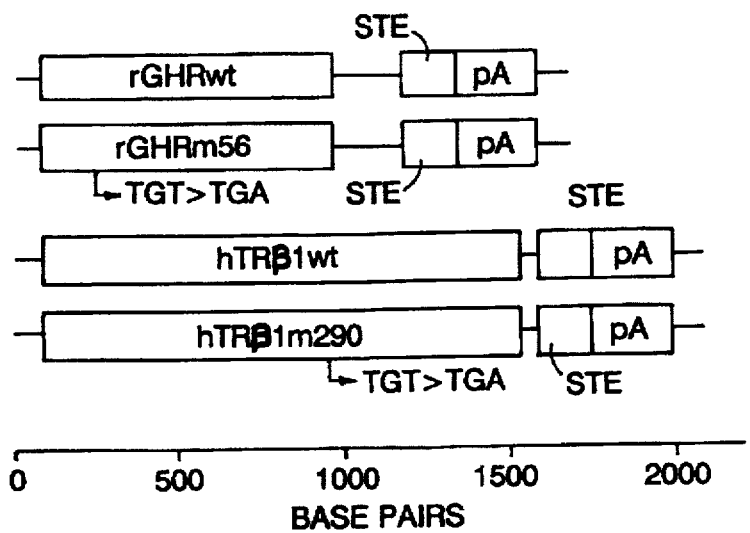
FIG. 7A is a schematic representation of cDNA.STE constructs using rat growth hormone receptor (rGHR) and human thyroid hormone receptor β1 (hTRβ1).

A small number of eukaryotic and prokaryotic proteins, including bacterial formate dehydrogenases, the mammalian glutathione peroxidase (GPx) family (Mullenbach et al., *Nucleic Acids Res.*15:5484, 1987; Chambus et al., *EMBO J.* 5:1221, 1986; Esworthy et al., *Arch. Biochem. Biophys.* 286:330, 1991; Takahashi et al., *Blood* 68: 640, 1986), type I iodothyronine 5'deiodinase (Berry et al. (1991) *Nature* 349, 438–440), and selenoprotein P (Read et al. (1990) *J. Biol. Chem.* 265, 17899–17905), belong to a unique group of polypeptides that contains the unusual amino acid selenocysteine.

The production of selenoproteins has been reported to be strictly regulated by the level of exogenous selenium. For example, Knight et al. (*J. Nutr.* 117:732, 1987) reported that glutathione peroxidase activity decreased to undetectable levels in rats given a selenium deficient diet (≦0.02 ppm, 0.016 mg/kg). Chanoine et al. (*Endocrinology* 131:1787, 1992) also reported that rats receiving a selenium deficient diet for six weeks had a significant decrease in both type I and type II 5'-deiodinase levels (≦20% normal). Speier et al. (*J. Biol. Chem.* 260:8951, 1985) demonstrated that, in vitro, glutathione peroxidase activity depended on a selenium concentration in the medium of more than 1 ng/ml, with an optimal activity observed at 5 ng/ml sodium selenate (2.6× $10^{-8}$M), whereas cells grown in medium without Se supplementation became glutathione peroxidase deficient, with only 1–3% of the activity of Se-supplemented cells. Chada et al. (*Blood* 74:2535, 1989) and Chu et al. (*Nucleic Acids Res.* 18:1531, 1990) also reported a 30 to 50 fold difference in glutathione peroxidase activity between selenium deficient and selenium replete cells.

The control of selenoprotein production by exogenous selenium is believed to occur by post-transcriptional regulation by the incorporation of selenocysteine cotranslationally at a UGA codon (Böck et al. (1991) *Trends Biochem. Sci.* 16, 463–467), which normally acts as a translational stop codon, through the utilization of a unique selenocysteine-charged tRNA containing the appropriate UCA anticodon (Hawkes et al. (1982) *Biochim. Biophys. Acta* 699, 183–191; Lee et al. (1989) *J. Biol. Chem.* 264, 9724–9727). Thus, regulation of selenoproteins most likely proceeds by control of the translation process at the mRNA UGA codon. Selenium incorporated into a selenocysteinyl-tRNA allows translational read through whereas, in the absence of selenium, the selenocysteine tRNA would remain unacylated and the UGA codon would then function to terminate translation.

Since the first identification of the use of the UGA codon for selenocysteine incorporation, a critical question in the interpretation of this "extended genetic code" is how the ribosomal translation assembly can discriminate the special UGA codon in the open reading frame of a selenoprotein mRNA from the termination UGA codon in other mRNA species.

Determination of Specific Sequences Required in STEs

As described in our copending application U.S. Ser. No. 08/454,028, entitled "Post-Translational Gene Regulation By Selenium," filed on May 30, 1995, which is incorporated herein by reference, we have identified all of the elements necessary and sufficient to signal the translation of UGA as selenocysteine.

Our data demonstrate that small segments of the 3' untranslated region (3'UTR) of the human GPx gene, specifically the AUGA (loop I), UGAU (loop II), and conserved AAA (loop III) sequences within the STE, and not the stem-loop or hairpin structures in the coding region, are essential for selenocysteine translation in human GPx. Moreover, our data demonstrate that the GPx 3'UTR alone is sufficient to signal the translation, as selenocysteine, of an opal mutation (UGA) in the open reading frame of an unrelated non-selenoprotein, rab5b. The rab5b gene encodes a member of Ras-related GTPase superfamily (Wilson et al. (1992) *J. Clin. Invest.* 89, 996–1005).

To examine the contribution of individual conserved regions of the STE stem-loop structure to selenocysteine insertion into the mammalian growth hormone peroxidase (GPx) family, we tested three epitope-tagged human GPX1 cDNA constructs with deletions of the basal stem, the upper stem, and the non-conserved apical loop sequence of the wild-type GPx selenium translation element (FIG. 4A). Nucleotide numbering in FIG. 4A (SEQ ID NO:7) starts with the "U" at the 5' end of the stem-loop, which corresponds to nucleotide 935 of the GPX1 cDNA sequence (Mullenbach et al., *Nucleic Acids Res.*, 15:5484, 1987), and nucleotide 656 in the GPx sequence of FIG. 1.

Figure 5:
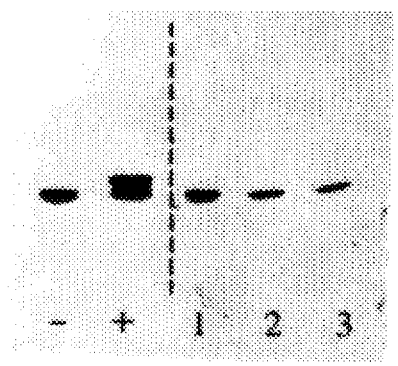
FIG. 5 is an autoradiograph of a representative SDS-PAGE of immunoprecipitated endogenous glutathione peroxidase (lower bands) and transfected, epitope-tagged glutathione peroxidase (upper bands), and shows the effects of deletions of the basal stem, upper stem, and the non-conserved apical loop sequences on the function of GPX1 STE.

FIG. 5 depicts a $^{75}$Se autoradiograph of a representative SDS-PAGE of immunoprecipitated (from transfected COS<1 cells) endogenous glutathione peroxidase (lower bands) and transfected, epitope-tagged glutathione peroxidase (upper bands). FIG. 5 shows the effects of deletions of the basal stem, upper stem, and the non-conserved apical loop sequences on the function of the GPX1 STE. Lane "−" contains a mock-transfected COS-1, which is a negative control; lane "+" contains a wild-type GPX1 STE, which is a positive control; lane 1 contains a basal stem deletion; lane 2 contains an upper stem deletion; lane 3 contains a non-conserved apical loop deletion.

The first lane (−) shows a single band representing endogenous GPx in COS-1 cells transfected with the vector, pCMV4, alone. The second lane (+) shows the slightly larger, epitope-tagged GPX1 gene product in cells transfected with a construct containing the wild-type GPX1 STE. However, this slower-migrating band was not detectable in lanes 1, 2, or 3, representing cells transfected with the three partial deletion constructs described above. Thus, each major structural feature of the stem-loop, specifically the basal and upper segments of the stem and the non-conserved apical loop, are essential for the function of GPX1 STE (see also Table 1).

We next tested whether STE function could be maintained in constructs that contained major changes in the primary nucleotide sequence of non-conserved portions of the stem-loop, but preserved its overall secondary structure. For that purpose, two epitope-tagged GPX1 cDNA constructs with mutations in its STE were made. In one, the right and left arms of the upper stem were exchanged; in the other, the non-conserved apical loop sequence of the STE was inverted. The FOLDRNA software program (Genetics Computer Group, Inc.) predicted that these mutations would not perturb the overall secondary structure.

Figure 6:
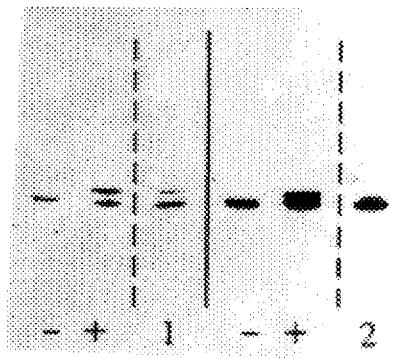
FIG. 6 is an autoradiograph of immunoprecipitated GPx showing the effects of stem exchange and apical loop inversion on the function of the GPX1 STE.

As shown in FIG. 6, when the stem exchange construct was expressed in COS-1 cells, epitope-tagged GPX1 expression reached levels comparable with the wild-type control construct (lane 1). Lane "−" contains a mock-transfected COS-1, which is a negative control; and lane "+" contains a wild-type GPX1 STE, which is a positive control. The apical loop inversion construct also directed selenocysteine incorporation into GSH-Px (lane 2), but quantitative measurements of the level of expression indicated that the level of expression was only 56–72% of that provided by the wild-type STE (see also Table 1).

Thus, the overall secondary structure of these segments appears sufficient to permit translation of the coding region UGA as selenocysteine, but some specific sequence or steric information in the non-conserved portion of the apical loop may also be important for STE function.

We further examined the role of specific nucleotide sequences in three very short, 2–4 nucleotide highly-conserved sequences in the GPX1 STE ($A_{21}U_{22}G_{23}A_{24}$, $A_{37}A_{39}A_{40}$, and $U_{60}G_{61}$, see FIG. 4A). Single and double nucleotide substitutions were performed in these conserved sequences and examined for their functional effects on the transient expression of epitope-tagged GPX1 in COS-1 cells. In parallel, we used a computer to analyze the possible secondary structure perturbations caused by each substitution. The results are summarized in Table 1 and described below.

TABLE 1

Effects of mutations in the GPX1 STE on selenocysteine incorporation into epitope-tagged glutathione peroxidase

| Mutation | Relative GPX1 Expression (%)[a] | Predicted Perturbation of Secondary Structure[b] |
|---|---|---|
| upper stem deletion[c] | 0,0 | yes |
| basal stem deletion[d] | 0,0 | yes |
| non-conserved loop deletion[e] | 0,0 | yes |
| upper stem exchange[f] | 100,106 | no |
| non-conserved loop inversion[g] | 72,56 | no |
| AAA→GAA | 38,30 | no |
| AAA→ACA | 35,89 | no |
| AAA→AGA | 98,92 | no |
| AAA→AUA | 39,77 | no |
| AAA→GAA | 38,30 | no |
| AAA→AA_ | 72,61 | no |
| AAA→AGG | 57,33 | no |

TABLE 1-continued

Effects of mutations in the GPX1 STE on selenocysteine incorporation into epitope-tagged glutathione peroxidase

| Mutation | Relative GPX1 Expression (%)[a] | Predicted Perturbation of Secondary Structure[b] |
|---|---|---|
| AAA→CAU | 0,0 | yes |
| AAA→GAU | 0,0 | no |
| UG→CG | 54,60 | no |
| UG→UA | 40,44 | no |
| UG→AA | 0,0 | yes |
| AUGA→AGGA | 0,0 | yes |
| AUGA→AUCA | 0,0 | yes |
| AUGA→AUGC | 0,0 | yes |
| AUGA→AUGG | 108,112 | no |
| AUGA→AUGU | 77,59 | no |
| AUGA→GGGA | 0,0 | yes |
| AUGA→UCGA | 0,0 | yes |

In Table 1, levels of selenocysteine incorporation were relative to simultaneous control transfection of epitope-tagged GPX1 with the wild-type 3'UTR (note a). The two numbers in the middle column represent the percentages of wild-type expression from two separate experiments. Computer analysis to predict the perturbations of the secondary structure was done using the FOLDRNA program of the Genetics Computer Group, Inc., software package (note b). The upper stem deletion was of nt 26–37 and 49–59 in FIG. 4A (SEQ ID NO:7) (note c). The basal stem deletion was of nt 1–20 and 68–86 in FIG. 4A (note d). The non-conserved loop deletion was of nt 41–48 in FIG. 4A (note e). The upper stem exchange was a complementary exchange of 3' and 5' sides (nt 26–37 and 49–59 respectively) of the upper stem in FIG. 4A (note f). The non-conserved loop inversion was of nt 41–48 in FIG. 4A (note g). Nucleotide numbering in Table 2 (and FIG. 4A) starts with the "U" at the 5' end of the stem-loop, corresponding to nucleotide 935 of the cDNA sequence (Mullenbach et al. 1987), and nucleotide 656 in the sequence of GPx in FIG. 1. All results represent duplicate independent experiments.

For the non-conserved apical loop region conserved sequence, AAA (FIG. 4A), we obtained four single- and three double-nucleotide substitutions by random oligonucleotide-directed mutagenesis. Expression of epitope-tagged GPX1 expression in COS-1 cells transfected with individual substitution constructs, compared with the wild-type STE, showed that most of the single nucleotide substitutions, as well as a single nucleotide deletion and one double nucleotide substitution, AAA→AGG, resulted in varying degrees of partial loss of selenocysteine incorporation activity. However, the other two double nucleotide substitutions, AAA→CAU (FIG. 4B) and AAA→GAU, caused a total loss of the function. Base pairing of the first C of CAU with nucleotide 49-G adds a base pair in the upper stem and reduces the size of the apical loop. One point mutation, AAA→AGA, preserved normal function, indicating some tolerance for substitution even within this highly conserved sequence.

A similarly wide range of effects was found with nucleotide substitutions in the second conserved sequence UG. The single base mutations UG→CG and UG→UA resulted in a loss of about 50% of selenocysteine insertion function, and the double substitutions of UG→AA and UG→GU (FIG. 4C) resulted in a total loss of GPX1 translation. The latter substitution causes the loss of a base pair between the nucleotide 25-G and the substituted 60-U, plus two new base-pairings: 25-G with 64-C and 24-A with 65-U, with a resultant disruption of the mid-stem "bubbles." Thus, STE function in the GPX1 gene can tolerate most single nucleotide mutations in these two conserved sequences, but is greatly diminished by additional substitutions.

The function of GPX1 STE was more sensitive to nucleotide substitutions in the third conserved sequence, AUGA. The AUGA→AGGA substitution is shown in FIG. 4D.

As shown in Table 1, five single substitutions for each of the first three nucleotides, as well as two double substitutions in this region, all resulted in a total loss of STE function. In the last conserved nucleotide of the short sequence, substitutions of G and U for the wild-type 24-A had no major effect on function; but the substitution of C for the 24-A totally abolished selenocysteine incorporation.

These results confirm the previous deletion experiments in the demonstration of the importance of the three short conserved nucleotide sequences for STE function. However, the substitution mutations also indicate differences in the apparent stringency of the requirements for each sequence element. Reading of the 5' stem conserved sequence AUGA appeared to be the most stringent, with no tolerance for substitutions in the first three bases. The requirement for the apical loop conserved sequence AAA was less stringent, since a single nucleotide deletion and all single and even one double substitution were tolerated to some degree.

To evaluate the effects of the small sequence changes on secondary structure of the STE we examined the predicted structure of the 87-nucleotide STE segment by FOLDRNA program analysis of each mutation (Table 1 and FIGS. 4A to 4D).

For mutations of the AAA sequence segment, computer analysis predicted that only one of the mutations, the double substitution CAU, resulted in a local secondary structure perturbation. As shown in FIG. 4B, this construct allowed formation of an additional base pair on the top of the upper stem, between the first C of CAU and nucleotide 49-G at the 3' end of the non-conserved apical loop sequence (nucleotide numbering in this figure starts with the "U" at the 5' end of the stem-loop, corresponding to nucleotide 935 of the GPX1 cDNA sequence (Mullenbach et al., 1987), and nucleotide 656 of FIG. 1.

For the conserved UG sequence, the FOLDRNA program predicted that both of the double substitutions that inhibit STE function, but not the innocuous single substitutions, would cause a local perturbation of the secondary structure at the mid-stem bulge. As shown in FIG. 4C, the double substitutions caused a loss of a base pair between the nucleotide 25-G and the substituted 60-U, plus two new base-pairings between 25-G and 64-C and between 24-A and 65-U. Nucleotide 24-A is part of the conserved sequence AUGA that is normally unpaired in the wild-type GPX1 STE.

For mutations within the third conserved sequence, computer analysis further predicted that all the detrimental single- and double substitutions for the first three nucleotide A, U, and G, plus the single substitution of C for the last nucleotide A, resulted in local secondary structure perturbations (Table 1 and FIG. 4D); whereas the innocuous single substitutions of G or U for the last nucleotide A did not alter the local secondary structure.

These results indicate a strong correlation between the functional effects of nucleotide substitutions within the three short conserved sequences of the GPX1 STE and their effects on the secondary structure of the stem-loop. Mutations that perturbed the secondary structure of the stem-loop and its mid-stem bulge profoundly affected STE function, but sequence changes that preserved secondary structure had little or no effect on selenocysteine incorporation. The only exception to the latter rule were mutations in the conserved apical loop sequence, AAA (e.g. AAA→GAA, AAA→GAU).

"Optimized" Synthetic Selenocysteine Insertion Sequences

Examination of the genes encoding various known mammalian selenoproteins indicates that the 3'UTRs have little primary sequence similarity, but have similar potential stem-loop structures (Hill et al., J. Biol. Chem. 266:10050, 1991; Zinoni et al. Proc. Natl. Acad. Sci. 87:4660, 1990; Ho et al. Nucleic Acids Res. 16:5207, 1988; Berry et al., Nature 353:273, 1991). This lack of homology between the 3'UTRs of these genes combined with our analyses of the 3'UTR of human glutathione peroxidase, which have demonstrated that three 2 to 4 nucleotide stretches of the putative stem-loop structure are essential for selenocysteine incorporation, have allowed us to design synthetic nucleotide sequences that are capable of forming a stem-loop structure (STE) that contains the essential elements.

This "optimized" synthetic sequence contains a stem-loop containing a "bubble" 16 nucleotides from the base of the stem-loop (the lower stem), followed by an additional 11 nucleotide stem (the upper stem) with an 11 nucleotide apical loop, or balloon, at the top of the structure. The structure of this optimized STE is shown in FIG. 2 (SEQ ID NO:5). In this figure, N is any nucleotide; N:N is any pair of complementary nucleotides; $_xN:N_x$ is any number of pairs of complementary nucleotides; Y is U or C; R is G or A; V is any nucleotide except thymidine (T) or uracil (U); and MRS denotes a multiple restriction site for ease of insertion of the element into any appropriate cloning vector. The key nucleotides are in bold type.

A nucleotide sequence containing the elements of this optimized stem-loop can be constructed by standard techniques known to those skilled in the art of molecular biology. For example, we have synthesized such a synthetic stem-loop, as shown in FIG. 3 (SEQ ID NO:6), as follows. We synthesized four overlapping oligonucleotides comprising the "loop-bubble-balloon" structure of the STE of GPx using an Applied Biosystems DNA synthesizer and 5'-phosphates were added by polynucleotide kinase. The four oligonucleotides comprising the sense and complementary strands of the stem loop were:

1) Sense Strand (nucleotides 1–50)(SEQ ID NO:8)

5'-CCTAGGAAGAGCTCCACCATAAAAGAAT-
GAGCCACAAGGAGGAAACCTAC-3'

2) Sense Strand (nucleotides 51–102) (SEQ ID NO:9)

5'-GAGTCTCCTTTGTGGTGATCTTACTC-
TACTTTTGGGGGGGCTCTTCTAGAC-3'

3) Complementary Strand (nucleotides 105–61) (SEQ ID NO:10)

5'-TCGAGTCTAGAAGAGCCCCCCCAAAAG-
TAGAGTAAGATCACCACA-3'

4) Complementary Strand (nucleotides 60–4) (SEQ ID NO:11)

5'-AAGGAGACTCGTAGGTTTCCTCCTTGTG-
GCTCATTCTTTTATGGTGGAGCTCTTCCTAGG3'

After gel purification, these four single-stranded oligonucleotides were annealed and the adjacent ends ligated with T4 DNA ligase. The resultant 105 double-stranded cDNA with AvrII and XbaI 4-base pair overhangs (as shown in FIG.

3; SEQ ID NO:6) was ligated into the XbaI site of pBluescript, and transformed into XL-1Blue cells. The sequence of the construct was determined by standard dideoxy sequencing strategy.

As shown above, the four-base sequence forming LOOP I (5'-AUGA-3') present on the first part of the apical non-conserved loop tolerates any purine in the second position. Similarly, the base-paired stems can be reversed without consequence. Thus, as shown in FIG. 2, optimized stem-loop STEs capable of efficient translation of the codon UGA for selenocysteine incorporation can be synthetically produced using the following parameters:

(1) The stem structure of the STE must have a minimum of 8 base-paired nucleotides ("base stem") followed by an additional stretch of base-paired nucleotides ("lower stem") that can tolerate two to four, one to two nucleotide non-complementary base interruptions, such that the base stem is at least 16 base-pairs in length.

(2) LOOP I is comprised of the sequence 5'-AUGRG-3' (SEQ ID NO:2) where R is either an adenine (A) or guanine (G), and the -UG- dinucleotide sequence is capable of pairing with complementary nucleotides contained in LOOP II.

(3) LOOP III (the non-conserved apical loop sequence) is composed of a stretch of 11 non-complementary nucleotides with the sequence 5'-ARANNNNNNNN-3' (SEQ ID NO:4), where R is either an adenine (A) or guanine (G), necessary for stem loop function.

(4) LOOP II is composed of 9 nucleotides with the sequence 5'-YRNNNNUAV-3' (SEQ ID NO:3), where Y is either a cytosine (C) or uracil (U), R is either adenine (A) or guanine (G), and the V is any nucleotide except thymidine (T) or uracil (U). The -UA- dinucleotide is complementary to the -UG- dinucleotide in LOOP I with U pairing with G and the A pairing with U. Guanine has the property of hydrogen bonding with all nucleotides.

By simple examination of other combinations of these base degeneracies, optimized stem loops (STEs) other than the one in FIG. 3 can be synthetically synthesized.

Construction of Recombinant Selenocysteine-containing Polypeptides

We have developed a system for the controlled insertion of selenocysteine into heterologous proteins that exploits the requirement for a 3' UTR STE to direct the incorporation of selenocysteine at a specific UGA codon. Translation of a target cDNA with one or more selenocysteines at specific locations is achieved by mutating either one or more specific codons that encode a non-essential amino acid or UGU, which encodes cysteine, to a UGA (or TGA), which encodes selenocysteine or termination, and then fusing the mutated coding region to either a synthetic STE, or to the STE from human cellular glutathione peroxidase. The method works for any desired polypeptide for which the DNA sequence is known.

The preparation of these "TGA" ("UGA") mutants is generally accomplished by site-directed or oligonucleotide based mutagenesis techniques, e.g., using commercially available kits (Promega). These techniques enable the user to precisely define where the UGA codon will be located, and thus where the SeCys residue will be located, in the resulting selenopolypeptide. For example, we have examined the levels of protein expression and the functional consequences of the introduced selenocysteine residue for two selenocysteine mutant proteins of known function, the circulating form of the rat growth hormone receptor (rGHR) and the human thyroid hormone receptor β1 (hTRβ1). As described in further detail below, the cDNA encoding the hTRβ1 was cloned into the multiple cloning site of the vector p-ALTER (Promega) and the cysteine codon at position 290 was mutated to TGA by oligonucleotide based mutagenesis. The cDNA was then rescued by standard laboratory procedure, and the mutation was confirmed by nucleotide sequencing.

Specifically, a 212 nucleotide restriction fragment containing the STE from the 3'UTR of the GPX1 gene provided the downstream stem-loop and sequence elements necessary to interpret UGA as a selenocysteine codon in the constructs shown schematically in FIG. 7A. A synthetic STE as described above and shown in FIGS. 2 and 3 can also be used. The AvrII-XbaI restriction fragment of the GPX1 gene (nt920-1132) containing the 3'UTR STE was ligated into the XbaI site of the expression vector pRC/CMV (Invitrogen) to generate pRC/CMV.STE. Orientation was confirmed by DNA sequencing.

The 1.2 kb rat adipocyte GHRs cDNA (Frick et al., *Endocrinology*, 131:3083–90, 1989) and the 1.7 kb human TRβ1 cDNA (Evans, *Science*, 240:889–95, 1988) were subcloned into the EcoR1 site of pALTER-1 and oligonucleotide-directed mutagenesis performed according to manufacturer's instructions (Promega). A coding region UGA (opal) mutant was generated by mutating the UGU (cysteine) codon to UGA at amino acid position 56 of rGHR (upper pair of constructs in the figure) and at amino acid position 290 of hTRβ1 (lower pair of constructs). The UGA (opal) mutants were confirmed by sequencing with the fmol DNA sequencing kit (Promega).

Constructs were completed by ligation of either opal or wild-type cDNAs into the BstXI site of pRC/CMV-STE. The opal mutant and wild-type cDNAs were inserted 5' to the STE sequence of the GPX1 gene and transcription was terminated by the bovine growth hormone polyadenylation signal in the eukaryotic expression vector pRC/CMV (Invitrogen). The integrity and orientation of each construct was confirmed by DNA sequencing.

Figure 7B:
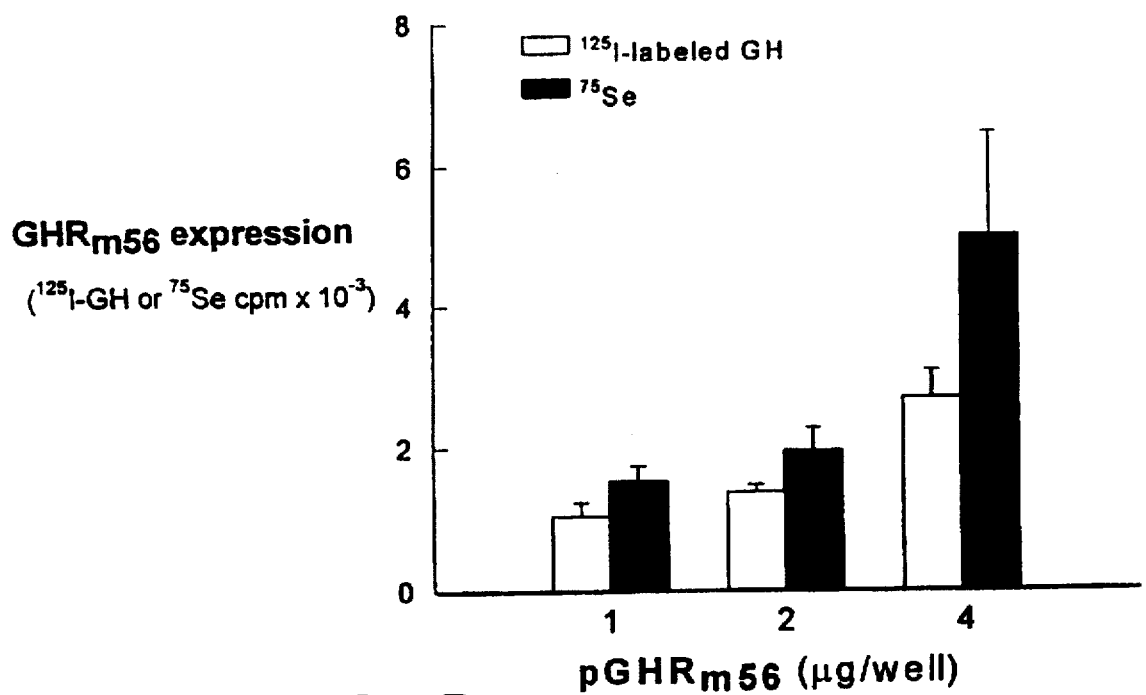
FIG. 7B is a graph showing expression of UGA (opal) mutant GHRs.

In transient expression assays done in COS7 cells, transfection of the opal mutant fusion construct rGHRm56.STE programmed the synthesis and secretion of a full-length, immunoprecipitable growth hormone receptor (FIG. 7B). COS7 cells (75,000 cells/well) were seeded into six well clusters plates (Costar) and transfected in triplicate with increasing amounts of pGHRm56. STE by the $CaPO_4$ coprecipitation as described in Chen et al., *Mol. Cell Biol.*, 7:2745–52 (1987). After 4 hours, the transfection medium was replaced with DMEM/F12 medium supplemented with insulin (20 µg/ml), transferrin (10 µg/ml), hydrocortisone (10 nM), bovine serum albumin (1 mg/ml), penicillin (50 U/ml), and streptomycin (90 µg/ml), and 40 nM $^{75}$Se as Na selenite (150 Ci/g). Cells were grown for 48 hours at 37° C. in a humidified atmosphere containing 5% $CO_2$. GHRs expression was determined in triplicate in 300 µl aliquots of medium by the method of Frick and Goodman, *Endocrinology*, 131:3083–90 (1989), and $^{75}$Se incorporation into the GHRs immuno-precipitate was determined by γ-counting. Data are reported in FIG. 7B as mean ±S.E (n=4).

Figure 7C:
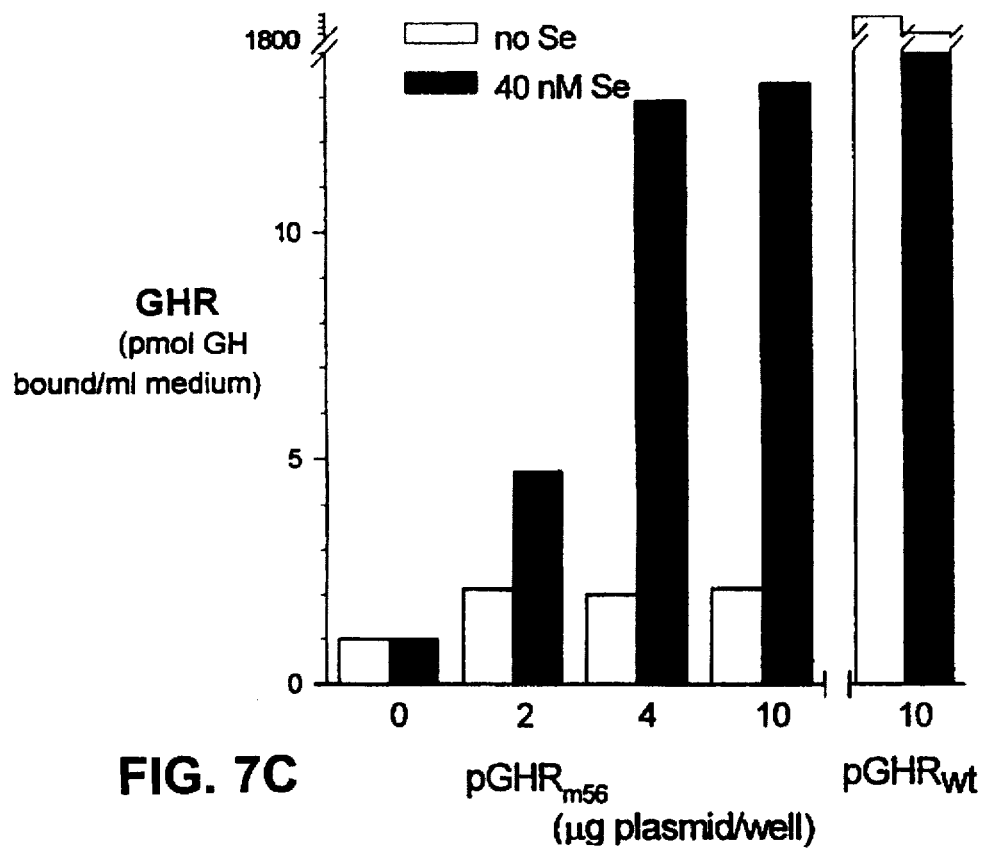
FIG. 7C is a graph showing selenium-dependent expression of opal mutant GHRs.

FIG. 7C shows selenium-dependent expression of opal mutant GHRs. Triplicate wells of COS7 cells were transfected as above with either pGHRm56.STE or pGHRwt.STE, grown for 48 hours in DMEM/F12 with or without 40 nM selenium, and GHRs determined as above. Data are reported as the mean of quadruplicate wells. Co-precipitation of $^{125}$I-labeled growth hormone (open bars) demonstrates that the opal mutant rGHRm56.STE construct retains ligand binding activity, and $^{75}$Se-labeling (hatched bars) of the immunoprecipitated rGHR indicates the incorporation of a selenoamino acid. Scatchard analysis (not shown) revealed that the opal mutation of rGHR did not affect ligand affinity; however, the number of opal rGHR molecules secreted into the culture medium was only 1–3% of that secreted by cells expressing the wild-type rGHR.STE construct. This finding was confirmed by the 30–100 fold greater expression of the wild-type receptor in transfected COS7 cells (FIG. 7C). While the STE is essential for expression of the opal mutant of the rGHR, the presence of the STE in the 3'UTR of the wild-type rGHR construct had little or no effect on the absolute expression levels of the wild-type receptor (data not shown).

As shown in FIG. 7C, expression of the opal mutant rGHRm56.STE construct was entirely dependent upon the presence of selenium in the culture medium. Since the anti-receptor antibody is directed against the C-terminus of the receptor, translation products truncated at amino acid 56 due, to the absence of selenium, are not detected in this functional assay. In contrast, selenium had no effect on expression of the wild-type rGHR.STE construct.

Figure 7D:
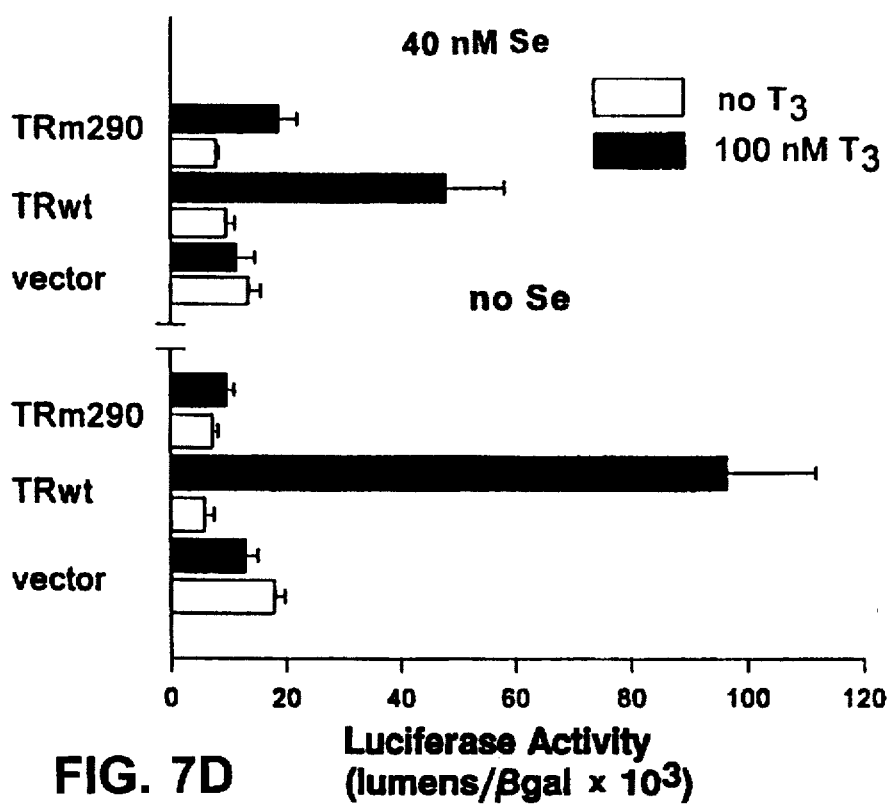
FIG. 7D is a graph showing selenium-dependent expression of functional opal mutant TRβ1.

We then examined the opal mutant of the human thyroid hormone receptor (hTRβ1) using a functional reporter assay that requires both ligand binding and signal transduction and transient expression of the hTRβ1.STE constructs. This heterologous reporter system uses a $T_3$-responsive reporter plasmid (pF2H-luc) as described in Spanjaard et al., Mol. Endocrinology, 8:286–95 (1993), consisting of a thyroid hormone response element (TRE) from the chick lysozyme gene ($TRE_{F2H}$), the inducible thymidine kinase (TK) promoter, and the luciferase reporter. The results obtained when pF2H-luc was co-transfected into COS7 cells along with the different thyroid hormone receptor constructs are shown in FIG. 7D. COS7 cells (50,000 cells/well) were seeded into 24 well cluster plates (Costar) and transfected by $CaPO_4$ coprecipitation with 0.5 µg pF2H-luc, 0.2 µg pRSVβgal (Promega), and 1 µg of either pRC/CMV.STE (vector), pTRwt.STE, or pTRm290.STE. After a 24 hour recovery period, medium was changed to DMEM/F12 medium ±40 nM selenium and ±100 nM $T_3$ (triiodothyronine) and cells were grown for an additional 72 hours. Luciferase and β galactosidase activities were determined using commercial kits according to manufacturer's instructions. Data are reported as the mean ±SE of quadruplicate wells.

Transient expression of the opal mutant of the thyroid hormone receptor, hTRm290.STE, produced a thyroid hormone receptor capable of mediating the triiodothyronine (T3)-dependent increase in luciferase expression. Like the opal mutants of rGHR, the level of opal TR expression was below that of the wild-type transfectants, presumably due to lower receptor numbers.

The selenium-deficient state eliminates functional expression of the opal TR mutant, but has no effect on expression of the wild-type construct. Without selenium, both the opal mutant hTRm290.STE and wild-type TR.STE control repressed luciferase expression in the absence of $T_3$ when compared to the empty vector controls, due to the well-described dominant negative effect of an unliganded thyroid hormone receptor (Evans, 1988). Since polypeptide chain termination at amino acid 290 in the opal mutant of TR yields a polypeptide containing the DNA-binding domain of the receptor and lacking only the ligand binding domain, the truncated protein should be capable of binding to the TRE of $T_3$-responsive genes.

Thus, the opal mutant-STE fusion constructs of rGHR and hTR direct the selenium-dependent incorporation of seleno-cysteine at UGA codons, leading to the production of selenium-containing, functional receptor molecules. However, in the transient transfection experiments, the levels of heterologous protein expression fell well below the wild-type controls. This failure to synthesize similar amounts of polypeptide probably reflects the limiting supply of selenocysteine-charged $tRNA^{[Ser]Sec}$, relative to the demands of multiple plasmid copy number and the strong promoters used to over-express the introduced gene products. Alternatively, inefficient interpretation of the opal codon for selenocysteine incorporation may result from losses of a large fraction of the opal mutant mRNA by cytoplasmic editing enzymes that degrade RNAs containing nonsense codons.

Figure 8A:
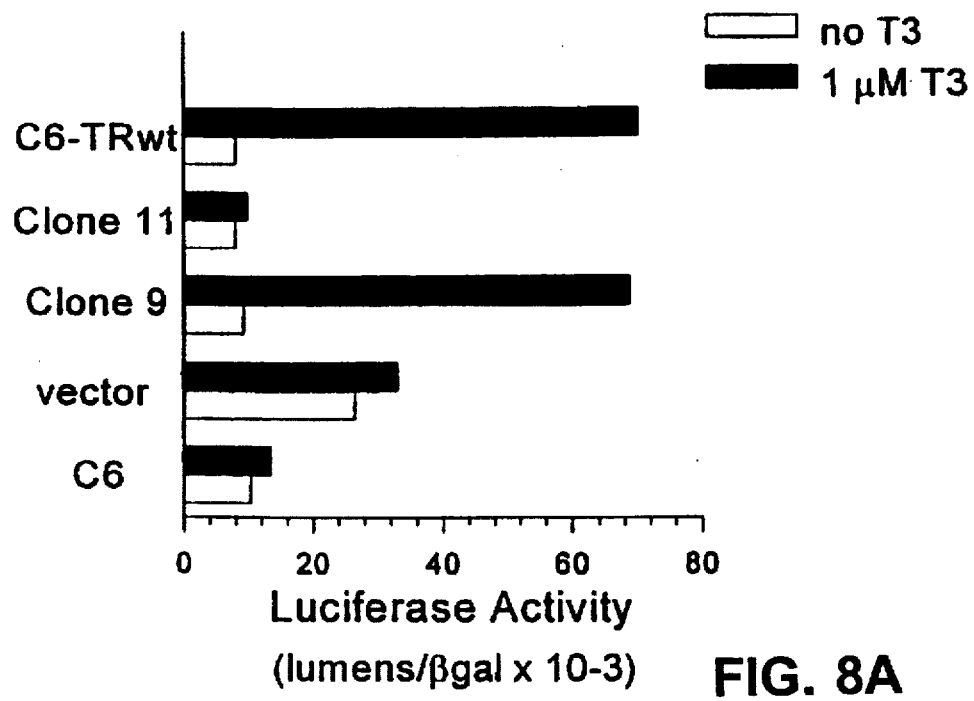
FIG. 8A is a graph identifying C6 cell lines that constitutively express the opal mutant of TRβ1.

Thus, stable transfections were used to evaluate the function of the TR opal mutant. FIG. 8A shows the expression of a functional thyroid receptor in selected clonal lines of rat C6 astrocytoma cells transfected with the opal mutant TRm290.STE construct. C6 astrocytoma cells (100,000 cells) were transfected by $CaPO_4$ coprecipitation with 10 µg of either pRC/CMV.STE (vector), pRC/CMV-TRwt.STE (TRwt), or pRC/CMV-TRm290.STE (TRopal). After a 24 hour recovery, medium was changed to growth medium (DMEM supplemented with 10% bovine serum, 15 mM HEPES buffer (pH 7.1), penicillin (50 U/ml and streptomycin (90 µg/ml) and antibiotics), and 200 µg/ml G418 (Gibco). After 14 days, individual colonies of G418 (neomycin)-resistant cells were isolated by limiting dilution in 96 well microtiter dishes in the presence of G418 (200 µg/ml). Fifteen G418-resistant cell lines were obtained for TRopal and 24-G418-resistant cell lines for TRwt. Vector cells were a pool of G418-resistant cells without clonal isolation.

TR expression was confirmed by transient transfection with the pF2H-luc reporter plasmid, and analysis of $T_3$-dependent reporter activity. Selected cell lines were seeded (50,000 cells) in quadruplicate into 24 well cluster plates and transfected with 0.2 µg of pF2H-luc and 0.2 µg pRSVβgal by $CaPO_4$ coprecipitation and grown for 72 hours in serum-free DMEM/F12±100 nM $T_3$. Luciferase and β-galactosidase activities were determined as described above.

As in the transient expression experiments, cells harboring the opal mutant TRm290.STE construct (clone 9) showed $T_3$-dependent luciferase expression and suppressed reporter expression in the absence of the $T_3$. Several neomycin-resistant C6 clones failed to express the opal TR mutant (e.g., FIG. 8A, Clone 11), presumably due to incomplete integration of a full length TR cDNA into the genome. The $T_3$-dependent C6 cell line, Clone 9, was used in all subsequent experiments.

Figure 8B:
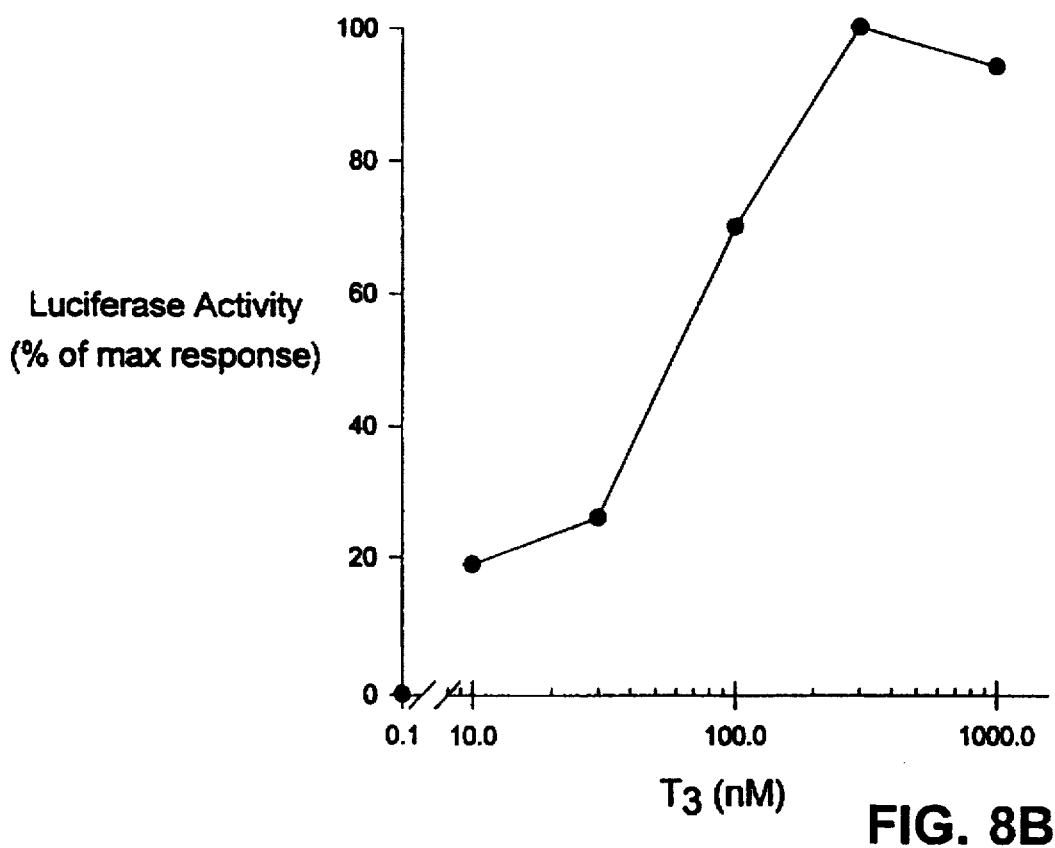
FIG. 8B is a graph showing $T_3$-dependent reporter expression in Clone 9 cells.

Clone 9 cells showed a normal dose-response relationship for $T_3$-dependent transactivation of reporter gene expression (FIG. 8B) suggesting adequate receptor affinity and number for the opal TR. Clone 9 cells (75,000 cells/well) were transfected by $CaPO_4$ co-precipitation with 0.2 µg pF2H-luc and 0.2 µg of pRSVβgal and cells grown in serum-free DMEM/F12 supplemented with increasing concentration of $T_3$ in triplicate. Reporter activities were determined as described above.

Figure 8C:
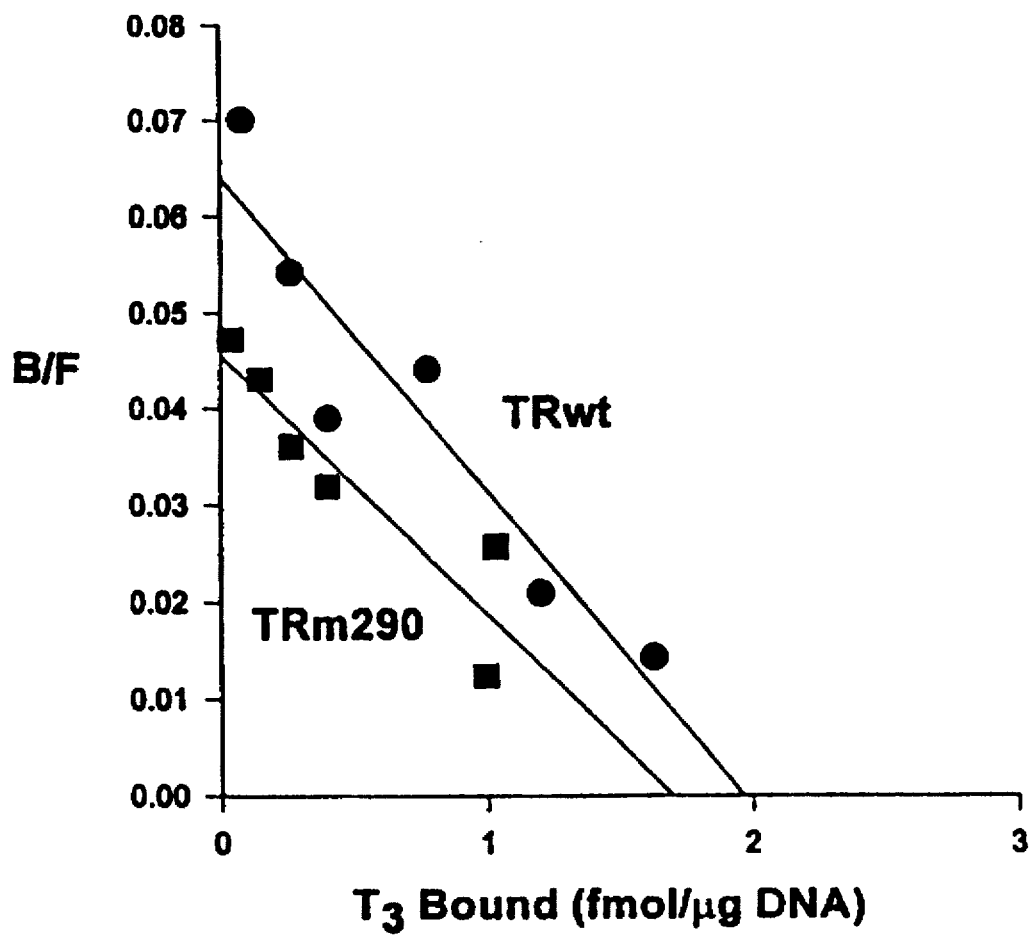
FIG. 8C is a Scatchard plot of nuclear $T_3$-binding in clone 9 and C6TRwt cells.

Scatchard analysis (FIG. 8C) of $T_3$ binding to isolated nuclei showed no significant difference between the ligand affinity or receptor number for the TRs derived from TRwt.STE or the opal mutant TRm290.STE constructs (Table 2). The selenium-dependent expression of the opal mutant TR protein in the clone 9 cells was confirmed by direct immunoprecipitation and by $^{75}$Se-labeling of nuclear proteins.

Clone 9 cells and C6TRwt were grown in four 80 cm² flasks to confluence, cell nuclei prepared as described in Ichikawa et al., Mol. Cell Endocrinology, 51:135–42 (1987), and TR determined by T₃-binding analysis. Each point of the Scatchard plot was determined in triplicate.

Table 2 presents an analysis of the quantity of nuclear TR in C6.TRwt and clone 9 cells. In Table 2, T₃ binding capacity was determined by Scatchard analysis. $^{75}$Se-labeled TR in Clone 9 cells was determined in 0.3M KCl extracts of isolated nuclei. Data are presented as the mean ±SE; the number in parentheses are the number of independent determinations.

TABLE 2

| cell line | integrated cDNA | T3 binding capacity (fmol/10⁶ cells) | $^{75}$Se-labeled TR (fmol/10⁶ cells) |
|---|---|---|---|
| C6•TRwt | hTRβ1•STE | 9.5 ± 3.4 (4) | ND |
| clone 9 | hTRm290•STE | 8.0 ± 2.0 (3) | 7.5 ± 1.2 (3) |

Figure 8D:
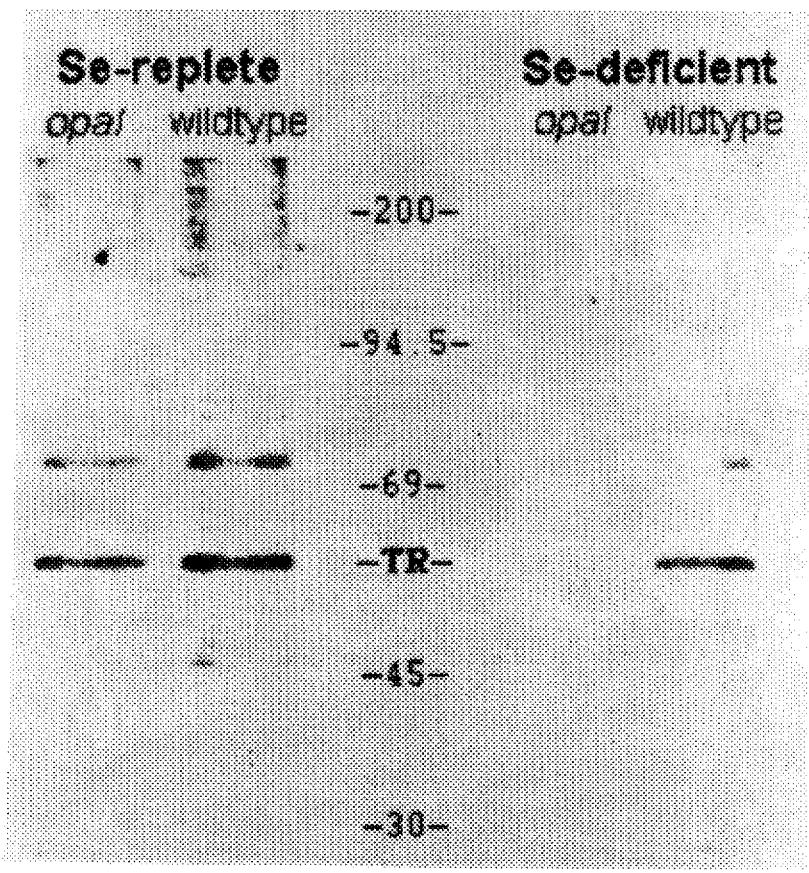
FIG. 8D is an autoradiograph showing selenium-dependence of nuclear TR localization.

SDS-PAGE analysis of anti-TRβ1IgG immunoprecipitated (FIG. 8D) shows that the opal mutant TRm290 and TRwt fusion constructs produce approximately equal amounts of receptor protein in selenium-replete medium; no immunoreactive TR was found for clone 9 cells grown in the absence of selenium. Clone 9 and C6TRwt cells were grown in triplicate in 25 cm² flasks to ~80% confluence. Culture medium was changed to serum-free DMEM/F12±40 nM Se for 2 days. In selected flasks 40 nM $^{75}$Se (150 Ci/g) was added. Six hours before harvest, the medium was changed to serum-free DMEM/F12 containing 10 µCi/ml $^{35}$S-MET and the cells were labeled for 6 hours. Cell nuclei were prepared as before, TR extracted with 0.3M KCl, and immunoprecipitated with anti-TRβ1 IgG. Immunoprecipitates were resolved by SDS-PAGE under reducing conditions and radioautography performed.

Expression of the chromatin-associated, $^{75}$Se-labeled TR present in the clone 9 cell nucleus was in close agreement with the estimates made by ligand binding Scatchard analysis (Table 2).

Finally, we examined the ability of the opal mutant TRm290.STE to transactivate a native gene using the expression of the T₃-dependent, glial cell gene, myelin basic protein. As shown in FIGS. 9A to 9F, myelin basic protein expression showed normal T₃-dependence in clone 9 cells in the presence of selenium. Clone 9 and C6TRwt cells were grown on coverslips in serum-free DMEM/F12 medium supplemented ±40 nM Se and/or ±100 nM T₃ for 2 days. Cell monolayers were fixed with 4% paraformaldehyde and permeabilized with iced methanol. Myelin basic protein was visualized by indirect immunofluorescence using anti-myelin basic protein IgG from Boehringer-Mannheim, and Texas Red conjugated Goat anti-Rabbit IgG from Amersham.

Removal of selenium from the culture conditions led to the complete loss of T₃-dependent expression of myelin basic protein in clone 9 cells (FIGS. 9C and 9D), while the absence of selenium had no effect on T₃-dependent expression of this protein in control cells carrying the wild-type TR (FIGS. 9E and 9F). When 40 nM selenium was added to the culture medium clone 9 cells showed a full T₃-dependent expression of myelin basic protein (FIGS. 9A and 9B). Thus, hormone-dependent expression of the native gene, myelin basic protein, requires both T₃ and selenium in clone 9 cells that express the opal mutant of the TR, while changes in selenium availability had no effect on hormone responsiveness of this gene product in cells expressing the wild-type TR.

In these studies, selenium-dependent translation of two target cDNAs was conferred by conservative replacement of selenocysteine for cysteine using mutation of a UGU (encoding cysteine) to a UGA (encoding selenocysteine or termination), then fusion of the mutated coding region to a 3'UTR containing the STE from GPX1, a ubiquitous selenoprotein gene. The resultant opal rGHR.STE and opal hTR.STE constructs demonstrated selenium-dependent expression of each receptor, and the selenoprotein products maintained normal ligand binding and signal transduction capabilities. These findings definitively establish the ability of an STE in the 3'untranslated region of an mRNA to interpret a coding region UGA codon as a signal for selenocysteine incorporation rather than for chain termination, with preservation of function in gene products containing selenocysteine substitutions at selected sites. The system creates the potential for the general application of selenium-dependent translational control to the expression of a wide variety of target genes, and for site-specific heavy atom (selenium) substitution or $^{75}$Se radioisotopic labeling of the transfected gene products.

Expression of Selenopolypeptides

Polypeptides according to the invention can be produced by the expression of a recombinant nucleic acid having a sequence encoding the polypeptide linked to a recombinant nucleic acid containing a stem-loop structure required for translation of selenocysteine, using any appropriate expression system, e.g., transformation of a suitable eukaryotic host cell with the recombinant nucleic acid in a suitable expression vehicle such as those described above. Those skilled in the field of molecular biology will understand that any of a wide variety of expression systems can be used to provide a selenocysteine-containing recombinant protein of the invention.

For example, the cDNA encoding a desired polypeptide can be inserted into either of the eukaryotic expression vectors pcDNA1/neo and pRC/CMV (InVitrogen), which are especially preferred as parent vectors for the selenocysteine expression system of the invention, in an orientation designed to allow expression.

The precise host cell used is not critical to the invention. However, the eukaryotic cell is preferably a mammalian tissue culture cell, e.g., COS-1, HL-60, CV-1, C-6, LLC/PK-1, 3T3L1 or CHO cells, a yeast cell, e.g., *Saccharomyces cerevisiae*, or an insect cell, e.g., a cell line derived from *Spodoptera frugiperda* such as Sf9 and Sf21 cells, or *Trichoplusia ni*. Such cells are available from a wide range of sources (e.g., the American Type Culture collection, Rockland, Md.; InVitrogen Corporation, San Diego, Calif.; PharMingen Corporation San Diego, Calif.). The method of transformation or transfection, and the choice of expression vehicle, will depend on the nature of the polypeptide to be expressed and the host system selected. Transformation and transfection methods are described, e.g., in Ausubel et al. (eds.) *Current Protocols in Molecular Biology* (John Wiley & Sons, New York, 1994); expression vehicles can be chosen from those well-known in the art, e.g., in *Cloning Vectors: A Laboratory Manual* (P. H. Pouwels et al., 1985, Suppl. 1987).

Selenocysteine-containing polypeptides according to the invention can be produced by a stably-transfected mammalian cell line. A number of vectors suitable for stable transfection of mammalian cells are available to the public, e.g., see Pouwels et al., supra. Methods for constructing such cell lines are also publicly available, e.g., in Ausubel et al., supra.

In another alternative, for expression in yeast, the cDNA encoding a selenopolypeptide of the invention can be inserted into a yeast expression vector, e.g., a pRS vector from Stratagene Cloning Systems (La Jolla, Calif.) and transformed into yeast according to standard methods (see Ausubel et al. (eds.), supra.

In yet another alternative, for expression in insect cells, the cDNA encoding a selenopolypeptide of the invention can be inserted into an insect expression vector such as a baculovirus vector, and transformed into suitable insect cells according to known methods. See, e.g., Summers and Smith, *A Manual of Methods for Baculovirus Vectors and Insect Cell Culture Procedures*: Texas Agricultural Experimental Station Bulletin No. 1555 (College Station, Texas, 1988), and commercially available procedures as described in the InVitrogen Corporation Catalogue, San Diego, Calif. (1993), and the PharMingen Corporation Catalog, San Diego, Calif. (1993).

Once the desired selenopolypeptide is stably transfected into a host system, the production of the selenopolypeptide is induced at concentrations of selenium above 1 ng per ml. The optimal induction of selenopolypeptide production occurs at approximately 5 to 25 ng per ml medium with concentrations above 50 to 100 ng/ml being cytotoxic, depending on the cell type used.

Once the recombinant polypeptide is expressed, it can be isolated according to methods well known in the art and the functional activity can be determined by assays appropriate for the particular polypeptide, e.g., enzymatic activity or binding affinity. When the desired selenopolypeptide is expressed in cells that contain a native protein with the same functional activities, the selenopolypeptide can be distinguished from the native protein by its higher reactivity with nucleophilic agents due to the selenocysteine moiety as described in Leonard et al., *Biochim. Biophys. Acta* 787:122 (1984), or alternatively by radiolabeling with $^{75}$Se, as described herein.

Crystallographic Analysis of Selenopolypeptides

Once a selected polypeptide is created with one or more selenocysteines inserted at user-defined, specific locations in the polypeptide as described above, the resulting selenopolypeptide can be crystallized and analyzed to determine its three-dimensional structure. General methods for the preparation and analysis of polypeptide crystals have been disclosed. See, e.g., MacPherson, *Preparation and Analysis of Protein Crystals*, John Wiley & Sons (1982); Cantor, C. R. and Schimmel, P. R. *Biophysical Chemistry*, Chapters 13 and 14 (W. H. Freeman and Co., Oxford, Eng., 1980); and references cited therein.

In general, a selenopolypeptide crystal is useful for X-ray crystallography if it satisfies two criteria: 1) the crystal exhibits discrete maxima of spots at specific intervals, i.e., positions on the X-ray detector defined by Bragg's Law ($n\lambda=2d\sin\Theta$) and the unit cell parameters of the crystal; and 2) the crystal diffraction pattern exhibits a minimum Bragg spacing of $d \leq 3$ Å. A general discussion of Bragg's Law and the unit cell parameters of a crystal is found in Halliday and Resnick, *Fundamentals of Physics*, 2nd Ed. (John Wiley and Sons, Inc., 1981).

The method of MAD crystallographic analysis has been used for determining the structure of macromolecules which include selenium, for example, as selenomethionine, selenolanthionine, or selenobiotinyl streptavidin (Hendrikson, *Trans. Am. Crystallogr. Assoc.* 21, 11 (1985); Hendrickson, et al., *EMBO J.* 9, 1665 (1990); Hendrickson, *Science* 4, 91 (1991); Hendrickson, et al. *P.N.A.S., USA* 86, 2190 (1989), and references cited therein. This MAD analysis also can be used to determine the structure of a selenopolypeptide of the invention. Depending on the polypeptide, it may be desirable to combine MAD analysis with MIR to obtain accurate phases which can assist in the determination of crystallographic structure (see, for example, Ryu, et al., *Nature* 348, 419–423, 1990).

Selenium undergoes the same oxidation steps as those of sulfur, each resulting in a loss of electrons, yielding a family of heavy atoms that differ in the composition of their electron cloud. For example, a selenocysteine residue deep within hydrophobic regions of a polypeptide is less susceptible to oxidation than a selenocysteine residue located on the surface of the polypeptide. Such differences in oxidation state can be experimentally determined by MIR and/or MAD analysis of the relevant polypeptide crystal(s). The differences provide information about the location of the heavy atom in the three-dimensional structure of the protein. Using standard techniques, the selenocysteine can also be modified prior to crystal formation to form a selenide, selenoxide, seleninic acid, selenonic acid, selenone, or a seleno-sulfur group.

In particular polypeptides, the ability to position selenocysteine residues at will in a polypeptide can be used to introduce two such residues in positions that normally would be occupied by two cysteine residues that form a disulfide bridge. The two selenocysteine residues will form a diselenocystine bridge that is readily identifiable in the crystallized selenopolypeptide by MAD or MIR analysis. Once the bridge is identified, its position can be unambiguously determined to provide structural information about the polypeptide.

The ability to position selenocysteine residues at will also permits a family of selenopolypeptides to be produced, each with a selenocysteine located at a unique position in the polypeptide. Crystallization of each of these selenopolypeptides yields a family of crystals in which the heavy atom, selenium, is located at different known locations. X-ray crystallography and MAD and/or MIR analysis of this family of selenopolypeptide crystals will define the exact positions of the individual selenocysteine residues, again providing three-dimensional structural information about the polypeptide.

It is useful to know the structure of a polypeptide because it will provide immediate information regarding, for example: 1) the active site of the polypeptide (as in, for example, an enzyme), which is required to design synthetic binding partners that can bind with the active site of the enzyme, e.g., a transition state inhibitor; and 2) the surface properties of the polypeptide, which is required to design synthetic binding partners which bind with the polypeptide, e.g., antiviral drugs which bind a rhinovirus or an AIDS virus polypeptide, or a synthetic binding partner which mimics the activity of a naturally-occurring binding partner.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. A method for determining the structure of a heterologous polypeptide that does not contain selenocysteine in its native form, said method comprising (1) transfecting a cell with (i) a first nucleic acid encoding said polypeptide, wherein at least one, specific codon of mRNA transcribed from said first nucleic acid is replaced by the codon UGA, and (ii) a second nucleic acid operably linked to said first nucleic acid, said second nucleic acid directing the translation of said UGA codon as selenocysteine only when said cell can obtain selenium from the medium in which said cell is grown, wherein said second nucleic acid is derived from the 3' untranslated region of a gene encoding mammalian glutathione peroxidase and comprises a continuous stretch of at least 79 nucleotides comprising three stem elements, each having a 5' half and a 3' half, and three loop elements, each having a 5' end and a 3' end, wherein the stem elements comprise
 a) a base stem comprising at least 16 nucleotides that can form 8 complementary pairs of nucleotides,
 b) a lower stem comprising at least 16 nucleotides that can form 8 complementary pairs of nucleotides, the first nucleotide of the 5' half of the lower stem being bound to the last nucleotide of the 5' half of the base stem, and the first nucleotide of the 3' half of the lower stem being bound to the last nucleotide of the 3' half of the base stem, and
 c) an upper stem comprising at least 22 nucleotides that can form 11 complementary pairs of nucleotides, wherein the loop elements comprise
 d) a first loop consisting of 5'-AUGRG-3' (SEQ ID NO:2), the 5'-A being bound to the last nucleotide of the 5' half of the lower stem and the 3'-G being bound to the first nucleotide of the 5' half of the upper stem,
 e) a second loop consisting of 5'-YRNNNNUAV-3' (SEQ ID NO:3), the 5'-Y being bound to the first nucleotide of the 3' half of the upper stem and the 3'-V being bound to the last nucleotide of the 3' half of the lower stem, and
 f) a third, apical loop consisting of 5'-ARANNNN-NNNN-3' (SEQ ID NO:4), the 5'-A being bound to the last nucleotide of the 5' half of the upper stem and the 3'-N being bound to the last nucleotide of the 3' half of the upper stem, and wherein each A is adenine, G is guanine, N is adenine, guanine, cytosine, or uracil, R is guanine or adenine, U is uracil, V is any nucleotide except thymidine or uracil, and Y is uracil or cytosine;

(2) growing said cell in selenium-containing growth medium under conditions in which said cell incorporates at least one selenocysteine residue into said polypeptide at a specific location;

(3) isolating said polypeptide from said cell or said growth medium;

(4) forming a crystal of said polypeptide; and (5) performing X-ray crystallography on said crystal, wherein said selenocysteine residue is used to determine the structure of said heterologous polypeptide.

2. A method of claim 1, wherein at least two, specific codons of mRNA transcribed from said first nucleic acid are each replaced by the codon UGA, and wherein the cell incorporates at least two selenocysteine residues into said polypeptide at specific locations, at least two of the selenocysteine residues are combined to form a selenocystine residue, and said selenocystine residue is used to determine the structure of said polypeptide in the X-ray crystallography.

3. A method of claim 1, wherein prior to forming a polypeptide crystal, the selenocysteine residue has been modified to form a selenide, selenoxide, seleninic acid, selenonic acid, selenone, or a seleno-sulfur group, and wherein the modified selenocysteine residue is used to determine the structure of said polypeptide.

4. A method of claim 1, wherein the X-ray crystallography involves multi-wavelength anomalous diffraction analysis.

5. A method of claim 1, wherein X-rays used in the X-ray crystallography have wavelengths between about 0.3 to 3.0 Angstroms.

6. A method of claim 5, wherein said X-rays are produced by synchrotron radiation.

7. A method of claim 1, wherein said growth medium comprises at least 1 ng of selenium per milliliter.

8. A method of claim 1, wherein said second nucleic acid further comprises a first mutually exclusive multiple restriction site attached to the first nucleotide of the 5' half of the base stem and a second mutually exclusive multiple restriction site attached to the first nucleotide of the 3' half of the base stem.

9. A method of claim 1, wherein said second nucleic acid is synthetically derived, and comprises a continuous stretch of 87 nucleotides, wherein a) nucleotides 1 to 8 are complementary to nucleotides 87 to 80, respectively, and when base-paired together form a base stem consisting of 16 nucleotides in 8 complementary pairs of nucleotides,
 b) nucleotides 9 to 20 and 69 to 79 when base-paired together form a lower stem consisting of at least 8 complementary pairs of nucleotides,
 c) nucleotides 21 to 25 are 5'-$A_{21}U_{22}G_{23}R_{24}G_{25}$-3' (SEQ ID NO:2) and form a first loop,
 d) nucleotides 60 to 68 are 5'-$Y_{60}R_{61}N_{62}N_{63}N_{64}N_{65}U_{66}A_{67}V_{68}$-3' (SEQ ID NO:3) and form a second loop,
 e) nucleotides 26 to 37 and nucleotides 49 to 59 when base-paired together form an upper stem of at least 11 complementary pairs of nucleotides, and
 f) nucleotides 38–48 are non-complementary and are 5'-$A_{38}R_{39}A_{40}N_{41}N_{42}N_{43}N_{44}N_{45}N_{46}N_{47}N_{48}$-3' (SEQ ID NO:4) and form a third, apical loop, and wherein A is adenine, G is guanine, N is adenine, guanine, cytosine, or uracil, R is guanine or adenine, U is uracil, V is any nucleotide except thymidine or uracil, and Y is uracil or cytosine.

10. A method of claim 1, wherein said cell is an insect cell.

11. A method of claim 1, wherein said cell is a yeast cell.

12. A method of claim 1, wherein said cell is a mammalian cell.

13. A method of claim 1, wherein said method is used to detect a binding partner of said polypeptide.

14. A method of claim 1, wherein said second nucleic acid has the sequence of FIG. 2 (SEQ ID NO:5).

15. A method of claim 1, wherein said second nucleic acid has the sequence of FIG. 3 (SEQ ID NO:6).

16. A method of claim 1, wherein at least one of said UGA codons is introduced into said first nucleic acid by site-directed mutagenesis.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 832 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
GCGCC                                                                                               5

ATG TGT GCT GCT CGG CTA GCG GCG GCG GCC CAG TCG GTG TAT GCC                                        53
Met Cys Ala Ala Arg Leu Ala Ala Ala Ala Gln Ser Val Tyr Ala
 1               5                  10                  15

TTC TCG GCG CGC CCG CTG GCC GGC GGG GAG CCT GTG AGC CTG GGC TCC                                   101
Phe Ser Ala Arg Pro Leu Ala Gly Gly Glu Pro Val Ser Leu Gly Ser
             20                  25                  30

CTG CGG GGC AAG GTA CTA CTT ATC GAG AAT GTG GCG TCC CTC TGA GGC                                   149
Leu Arg Gly Lys Val Leu Leu Ile Glu Asn Val Ala Ser Leu SeC Gly
         35                  40                  45

ACC ACG GTC CGG GAC TAC ACC CAG ATG AAC GAG CTG CAG CGG CGC CTC                                   197
Thr Thr Val Arg Asp Tyr Thr Gln Met Asn Glu Leu Gln Arg Arg Leu
     50                  55                  60

GGA CCC CGG GGC CTG GTG GTG CTC GGC TTC CCG TGC AAC CAG TTT GGG                                   245
Gly Pro Arg Gly Leu Val Val Leu Gly Phe Pro Cys Asn Gln Phe Gly
 65                  70                  75                  80

CAT CAG GAG AAC GCC AAG AAC GAA GAG ATT CAG AAT TCC CTC AAG TAC                                   293
His Gln Glu Asn Ala Lys Asn Glu Glu Ile Gln Asn Ser Leu Lys Tyr
                 85                  90                  95

GTC CGG CCT GGT GGT GGG TTC GAG CCC AAC TTC ATG CTC TTC GAG AAG                                   341
Val Arg Pro Gly Gly Gly Phe Glu Pro Asn Phe Met Leu Phe Glu Lys
             100                 105                 110

TGC GAG GTG AAC GGT GCG GGG GCG CAC CCT CTC TTC GCC TTC CTG CGG                                   389
Cys Glu Val Asn Gly Ala Gly Ala His Pro Leu Phe Ala Phe Leu Arg
         115                 120                 125

GAG GCC CTG CCA GCT CCC AGC GAC GAC GCC ACC GCG CTT ATG ACC GAC                                   437
Glu Ala Leu Pro Ala Pro Ser Asp Asp Ala Thr Ala Leu Met Thr Asp
     130                 135                 140

CCC AAG CTC ATC ACC TGG TCT CCG GTG TGT CGC AAC GAT GTT GCC TGG                                   485
Pro Lys Leu Ile Thr Trp Ser Pro Val Cys Arg Asn Asp Val Ala Trp
145                 150                 155                 160

AAC TTT GAG AAG TTC CTG GTG GGC CCT GAC GGT GTG CCC CTA CGC AGG                                   533
Asn Phe Glu Lys Phe Leu Val Gly Pro Asp Gly Val Pro Leu Arg Arg
                 165                 170                 175

TAC AGC CGC CGC TTC CAG ACC ATT GAC ATC GAG CCT GAC ATC GAA GCC                                   581
Tyr Ser Arg Arg Phe Gln Thr Ile Asp Ile Glu Pro Asp Ile Glu Ala
             180                 185                 190

CTG CTG TCT CAA GGG CCC AGC TGT GCC TAG                                                           611
Leu Leu Ser Gln Gly Pro Ser Cys Ala AM
         195                 200

GGCGCCCCTC CTACCCCGGC TGCTTGGCAG TTGCAGTGCT GCTGTCTCGG GGGGGTTTTC                                 671

ATCTATGAGG GTGTTTCCTC TAAACCTACG AGGGAGGAAC ACCTGATCTT ACAGAAAATA                                 731

CCACCTCGAG ATGGGTGCTG GTCCTGTTGA TCCCAGTCTC TGCCAGACCA AGGCGAGTTT                                 791
```

CCCCACTAAT AAAGTGCCGG GTGTCAGCAA AAAAAAAAA A          832

( 2 ) INFORMATION FOR SEQ ID NO:2:

( i ) SEQUENCE CHARACTERISTICS:
    ( A ) LENGTH: 5 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:2:

AUGRG          5

( 2 ) INFORMATION FOR SEQ ID NO:3:

( i ) SEQUENCE CHARACTERISTICS:
    ( A ) LENGTH: 9 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:3:

Y RNNNNUAV          9

( 2 ) INFORMATION FOR SEQ ID NO:4:

( i ) SEQUENCE CHARACTERISTICS:
    ( A ) LENGTH: 11 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:4:

ARANNNNNNN N          11

( 2 ) INFORMATION FOR SEQ ID NO:5:

( i ) SEQUENCE CHARACTERISTICS:
    ( A ) LENGTH: 87 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:5:

NNNNNNNNNN NNNNNNNNNN AUGRGNNNNN NNNNNNNARA NNNNNNNNNN NNNNNNNNN Y          60

RNNNNUAVNN NNNNNNNNNN NNNNNNN          87

( 2 ) INFORMATION FOR SEQ ID NO:6:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( i i ) MOLECULE TYPE: RNA ( x i ) SEQUENCE DESCRIPTION: SEQ ID NO:6:

AGAGCUCCAC CAUAAAGAA UGAGCCACAA GGAGGAAACC UACGAGUCUC CUUUGUGGUG          60

AUCUUACUCU ACUUUGGGGG GGCUCU          86

( 2 ) INFORMATION FOR SEQ ID NO:7:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:7:

```
UCUCGGGGGG  GUUUUCAUCU  AUGAGGGUGU  UUCCUCUAAA  CCUACGAGGG  AGGAACACCU    60
GAUCUUACAG  AAAAUACCAC  CUCGAGA                                           87
```

( 2 ) INFORMATION FOR SEQ ID NO:8:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

```
CCTAGGAAGA  GCTCCACCAT  AAAAGAATGA  GCCACAAGGA  GGAAACCTAC    50
```

( 2 ) INFORMATION FOR SEQ ID NO:9:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

```
GAGTCTCCTT  TGTGGTGATC  TTACTCTACT  TTTGGGGGGG  CTCTTCTAGA  C    51
```

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

```
TCGAGTCTAG  AAGAGCCCCC  CCAAAAGTAG  AGTAAGATCA  CCACA    45
```

( 2 ) INFORMATION FOR SEQ ID NO:11:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

```
AAGGAGACTC  GTAGGTTTCC  TCCTTGTGGC  TCATTCTTTT  ATGGTGGAGC  TCTTCCTAGG    60
```